(12) United States Patent
Nagai et al.

(10) Patent No.: US 7,592,003 B2
(45) Date of Patent: Sep. 22, 2009

(54) REGULATION OF TOLL-LIKE RECEPTORS ON STEM CELLS

(75) Inventors: Yoshinori Nagai, Kanagawa (JP); Paul W. Kincade, Nichols Hills, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 123 days.

(21) Appl. No.: 11/537,200

(22) Filed: Sep. 29, 2006

(65) Prior Publication Data

US 2007/0087408 A1 Apr. 19, 2007

Related U.S. Application Data

(60) Provisional application No. 60/806,351, filed on Jun. 30, 2006, provisional application No. 60/722,174, filed on Sep. 30, 2005.

(51) Int. Cl.
*A61K 35/14* (2006.01)
*A61K 35/26* (2006.01)
*A61K 35/28* (2006.01)
*C07K 14/435* (2006.01)
*C07K 16/18* (2006.01)
*C12N 5/06* (2006.01)
*C12N 5/08* (2006.01)

(52) U.S. Cl. .................. 424/93.7; 424/93.1; 424/577; 435/375; 530/350; 530/387.1; 536/23.1

(58) Field of Classification Search .................. None
See application file for complete search history.

(56) References Cited

U.S. PATENT DOCUMENTS

| 7,312,320 B2 | 12/2007 | Elson ...................... 530/388.2 |
| 2004/0072347 A1 | 4/2004 | Schuler et al. ............... 435/372 |
| 2004/0259790 A1* | 12/2004 | Pulendran et al. ............. 514/12 |
| 2005/0163764 A1 | 7/2005 | Medzhitov et al. ........ 424/93.45 |
| 2007/0275890 A1* | 11/2007 | Johnson et al. ................ 514/12 |

FOREIGN PATENT DOCUMENTS

| WO | WO03012081 | 2/2003 |
| WO | WO-2004074435 A2 * | 9/2004 |
| WO | WO-2005067959 A1 * | 7/2005 |

OTHER PUBLICATIONS

Nagai et al. Toll-like receptors on hematopoietic progenitor cells stimulate innate immune system replenishment. Immunity 24(6): 801-812, 2006.*
Pulendran, B. Modulating vaccine responses with dendritic cells and Toll-like receptors. Immunol Rev 199: 227-250, 2004.*
LeBouder et al. Soluble forms of Toll-like receptor (TLR)2 capable of modulating TLR2 signaling are present in human plasma and breast milk. J Immunol 171(12): 6680-6689, 2003.*
Akashi et al., "A clonogenic common myeloid progenitor that gives rise to all myeloid lineages," *Nature*, 404:193-197, 2000.

Akashi et al., "Lipopolysaccharide interaction with cell surface Toll-like receptor 4-MD-2: higher affinity than that with MD-2 or CD14," *J. Exp. Med.*, 198:1035-1042, 2003.
Beutler, and Rietschel, "Innate immune sensing and its roots: the story of endotoxin," *Nat. Rev. Immunol.*, 3:169-176, 2003.
Blackwell and Krieg, "CpG-A-induced monocyte IFN-gamma-inducible protein-10 production is regulated by plasmacytoid dendritic cell-derived IFN-alpha," *J. Immunol.*, 170:4061-4068, 2003.
Divanovic et al., "Negative regulation of Toll-like receptor 4 signaling by the Toll-like receptor homolog RP105," *Nat. Immunol.*, 6:571-578, 2005.
Evans et al., "The use of Flt3 ligand as an adjuvant for hepatitis B vaccination of healthy adults," *Vaccine*, 21:322-329, 2002.
Ferrandon et al., "Sensing infection in *Drosophila*: Toll and beyond,"*Semin. Immunol.*, 16:43-53, 2004.
Hayashi et al., "Distinct osteoclast precursors in the bone marrow and extramedullary organs characterized by responsiveness to Toll-like receptor ligands and TNF-alpha,"*J. Immunol.*, 171:5130-5139, 2003.
Igarashi et al., "Transcription from the RAG1 locus marks the earliest lymphocyte progenitors in bone marrow,"*Immunity*, 17:117-130, 2002.
Iwasaki and Medzhitov, "Toll-like receptor control of the adaptive immune responses,"*Nat. Immunol.*, 5(10):987-995, 2004.
Iwasaki et al., "GATA-1 converts lymphoid and myelomonocytic progenitors into the megakaryocyte/erythrocyte lineages," *Immunity*, 19:451-462, 2003.
Iwasaki-Arai et al., "Enforced granulocyte/macrophage colony-stimulating factor signals do not support lymphopoiesis, but instruct lymphoid to myelomonocytic lineage conversion," *J. Exp. Med.*, 197:1311-1322, 2003.
Kadowaki et al., "Subsets of human dendritic cell precursors express different toll-like receptors and respond to different microbial antigens," *J. Exp. Med.*, 194(6):863-869, 2001.
Kim et al., "CpG oligodeoxynucleotides induce IL-8 expression in CD34+ cells via mitogen-activated protein kinase-dependent and NF-kappaB-independent pathways," *International Immunology*, 17(12):1525-1531, 2005.
Kondo et al., "Cell-fate conversion of lymphoid-committed progenitors by instructive actions of cytokines," *Nature*, 407:383-386, 2000.
Kondo et al., "Identification of clonogenic common lymphoid progenitors in mouse bone marrow," *Cell*, 91:661-672, 1997.

(Continued)

Primary Examiner—Bridget E Bunner
(74) Attorney, Agent, or Firm—Fulbright & Jaworski, LLP

(57) ABSTRACT

The discovery of Toll-like receptors (TLRs) on the surface of hematopoietic cells provides new methods for the stimulation and differentiation of various classes of progenitor cells. TLR2 and TLR4 agonists (natural ligands, mimetics, antibodies) are particularly useful in these methods. The cells can be isolated and used for various purpose including tissue regeneration and grafting. In contrast, antagonists of TLRs can be used to protect cells from various insults such as chemo- and radiotherapy, acute and chronic infection, and transplantation by inhibiting activation and differentiation. TLR2, TLR4 and TLR9 pathway antagonists (soluble TLR, mimetics, antibodies) are particularly useful in these methods. Cells can be isolated and used for various purposes including transplantation.

14 Claims, 17 Drawing Sheets

OTHER PUBLICATIONS

Kondo, et al., "Biology of hematopoietic stem cells and progenitors: implications for clinical application," *Annu. Rev. Immunol.*, 21:759-806, 2003.

Kouro et al., "Relationships between early B- and NK-lineage lymphocyte precursors in bone marrow," *Blood*, 100:3672-3680, 2002.

Liew et al., "Negative regulation of toll-like receptor-mediated immune responses," *Nat. Rev. Immunol.*, 5:446-458, 2005.

Means et al., "The CD14 ligands lipoarabinomannan and lipopolysaccharide differ in their requirement for Toll-like receptors," *J. Immunol.*, 163:6748-6755, 1999.

Nagai et al., "The radioprotective 105/MD-1 complex links TLR2 and TLR4/MD-2 in antibody response to microbial membranes," *J. Immunol.*, 174:7043-7049, 2005.

Oshiumi et al., "TICAM-1, an adaptor molecule that participates in Toll-like receptor 3-mediated interferon-beta induction," *Nat. Immunol.*, 4:161-167, 2003.

Rosmarin et al., "Transcriptional regulation in myelopoiesis: Hematopoietic fate choice, myeloid differentiation, and leukemogenesis," *Exp. Hematol.*, 33:131-143, 2005.

Sato et al., "MyD88 but not TRIF is essential for osteoclastogenesis induced by lipopolysaccharide, diacyl lipopeptide, and IL-1alpha," *J. Exp. Med.*, 200:601-611, 2004.

Seong and Matzinger, "Hydrophobicity: an ancient damage-associated molecular pattern that initiates innate immune responses," *Nat. Rev. Immunol.*, 4:469-478, 2004.

Sioud et al., "Signaling through toll-like receptor 7/8 induces the differentiation of human bone marrow CD34+ progenitor cells along the myeloid lineage," *J. Mol. Biol.*, 364:945-954, 2006.

Takeda and Akira, "Toll-like receptors in innate immunity," *Int. Immunol.*, 17:1-14, 2005.

Taylor et al., "Two-stage response to endotoxin infusion into normal human subjects: Correlation of blood phagocyte luminescence with clinical and laboratory markers of the inflammatory, hemostatic response," *Crit. Care Med.*, 29:326-334, 2001.

Tsan and Gao, "Endogenous ligands of Toll-like receptors," *J. Leukoc. Biol.*, 76:514-519, 2004.

Ueda et al., "Inflammation and the reciprocal production of granulocytes and lymphocytes in bone marrow," *J. Exp. Med.*, 201:1771-1780, 2005.

Ueda et al., "Inflammation controls B lymphopoiesis by regulating chemokine CXCL12 expression," *J. Exp. Med.*, 199:47-58, 2004.

Vermaelen and Pauwels, "Accurate and simple discrimination of mouse pulmonary dendritic cell and macrophage populations by flow cytometry: methodology and new insights," *Cytometry A.*, 61(2):170-177, 2004.

Xie et al., "Stepwise reprogramming of B Cells into macrophages," *Cell*, 117:663-676, 2004.

Yamamoto et al., "Role of adaptor TRIF in the MyD88-independent toll-like receptor signaling pathway," *Science*, 301:640-643, 2003.

Yoshimura et al., "Cutting edge: recognition of Gram-positive bacterial cell wall components by the innate immune system occurs via Toll-like receptor 2," *J. Immunol.*, 163:1-5, 1999.

Zhang et al., "Identification of the haematopoietic stem cell niche and control of the niche size," *Nature*, 425:836-841, 2003.

Zuniga et al., "Bone marrow plasmacytoid dendritic cells can differentiate into myeloid dendritic cells upon virus infection," *Nat. Immunol.*, 5:1227-1234, 2004.

PCT International Search Report and Written Opinion, issued in International Application No. PCT/US06/37853, dated Aug. 22, 2008.

Hollingsworth et al., "The critical role of hematopoietic cells in lipopolysaccharide-induced airway inflammation," *American Journal of Respiratory and Critical Care Medicine*, 171:806-813, 2005.

McCurdy et al., "Cutting edge: distinct toll-like receptor 2 activators selectively induce different classes of mediator production from human mast cells," *Journal of Immunology*, 170:1625-1629, 2003.

* cited by examiner

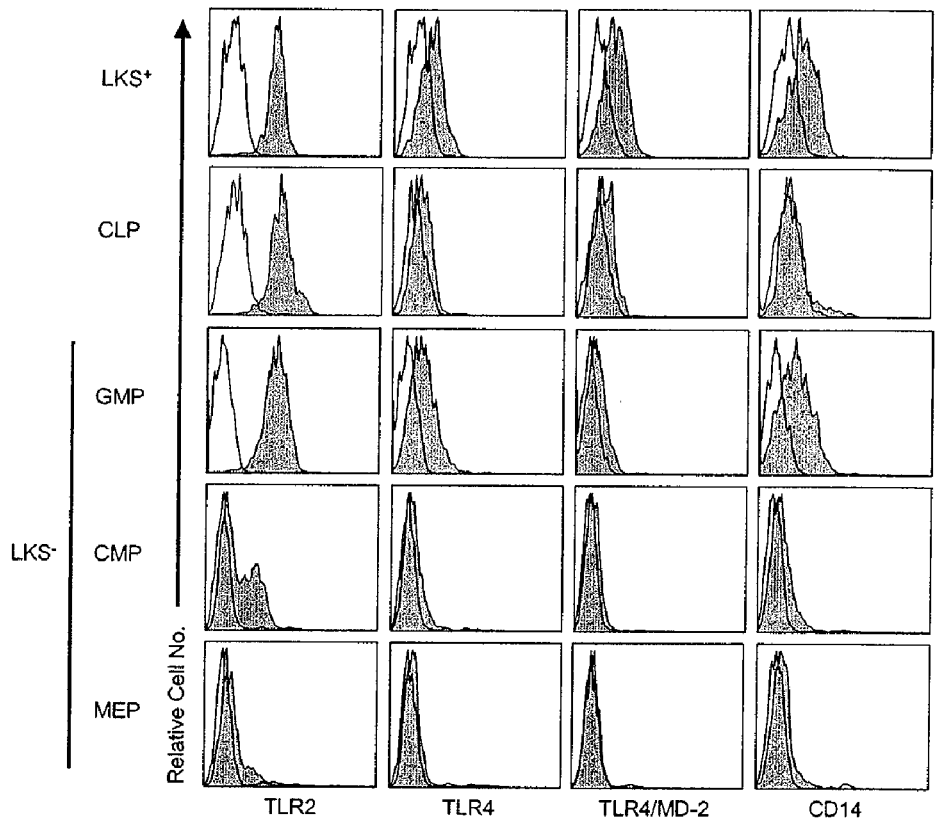
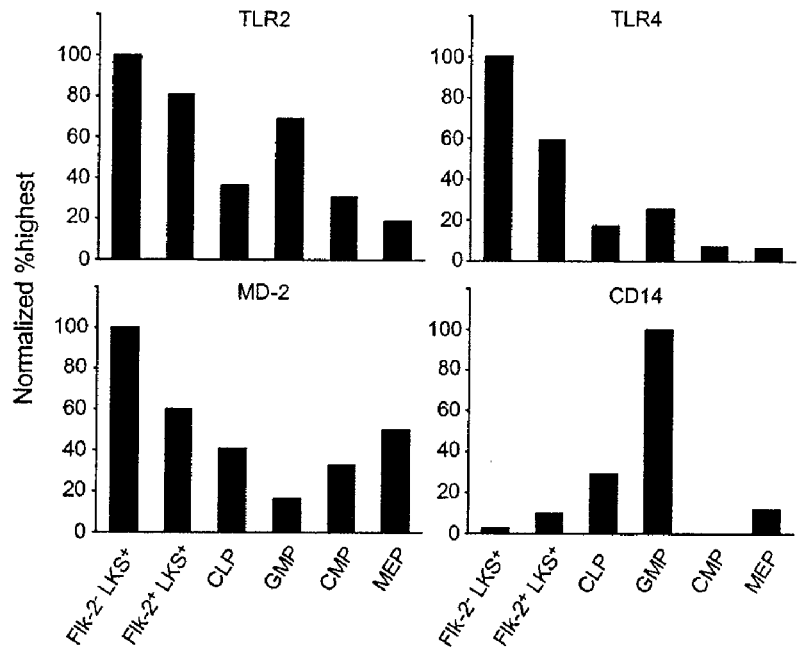
FIG. 1A-B

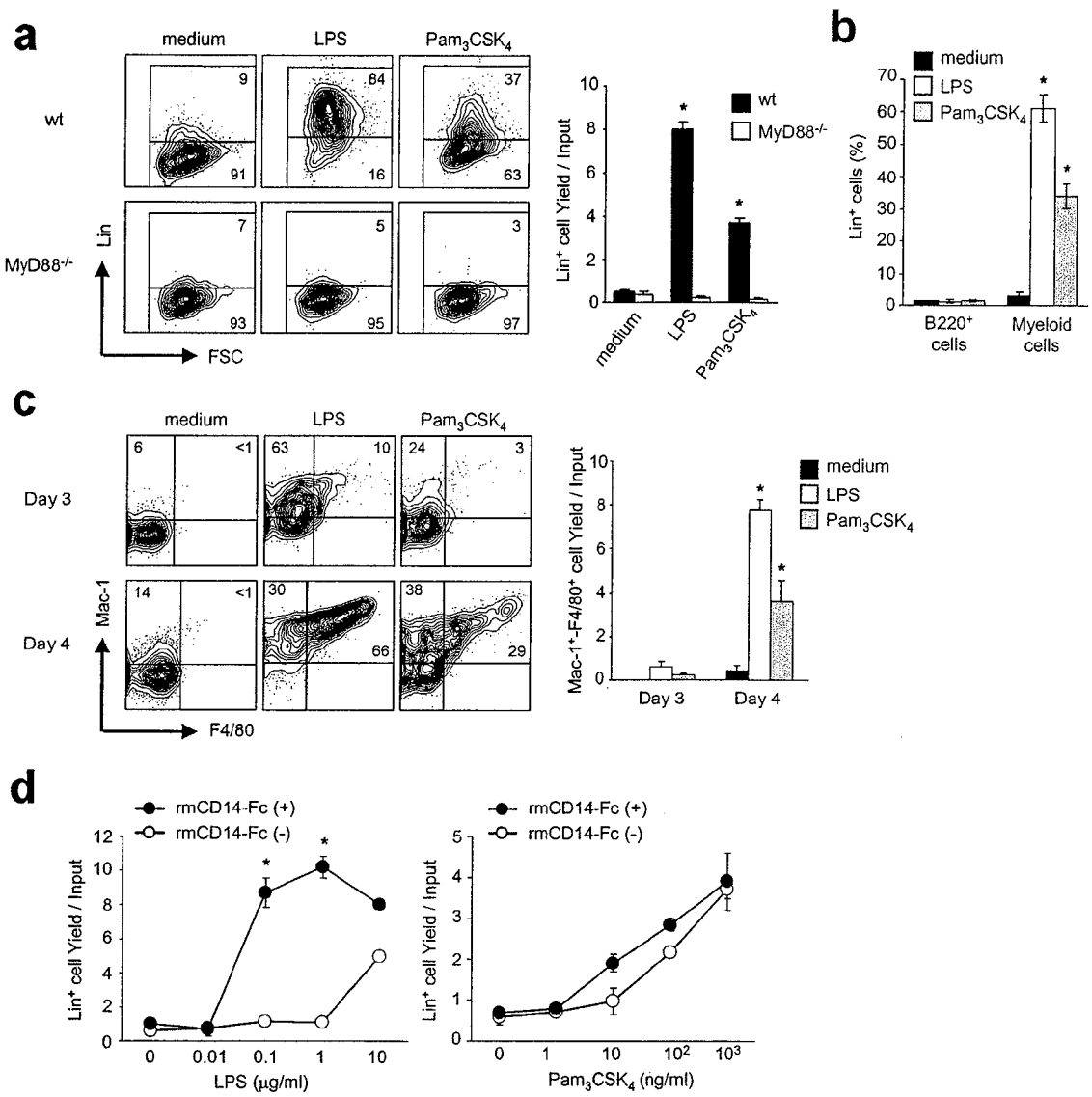
FIG. 2A-D

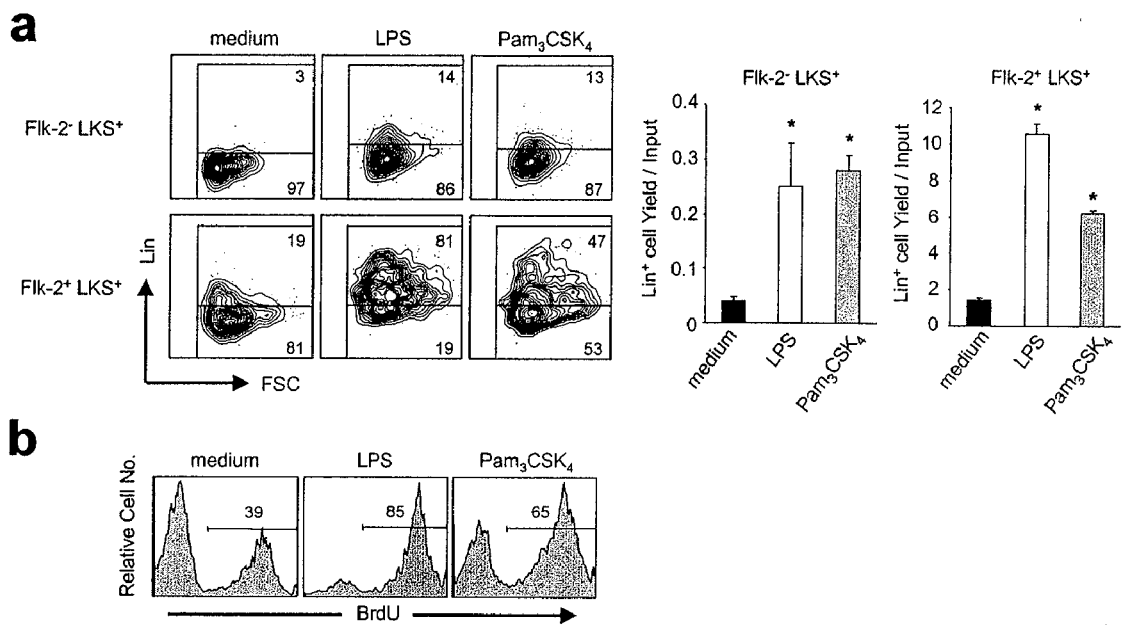
FIG. 3A-B

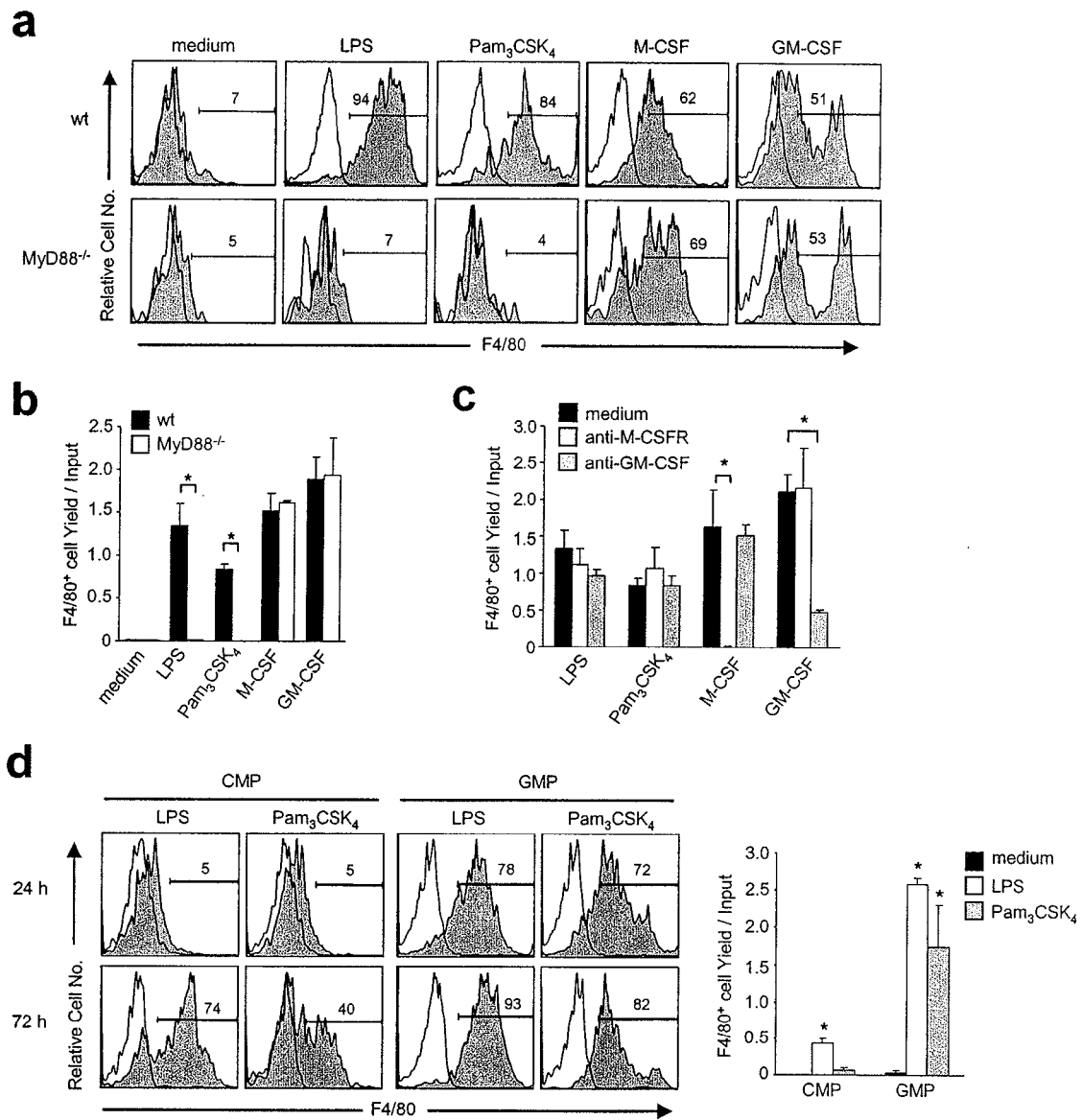
FIG. 4A-E

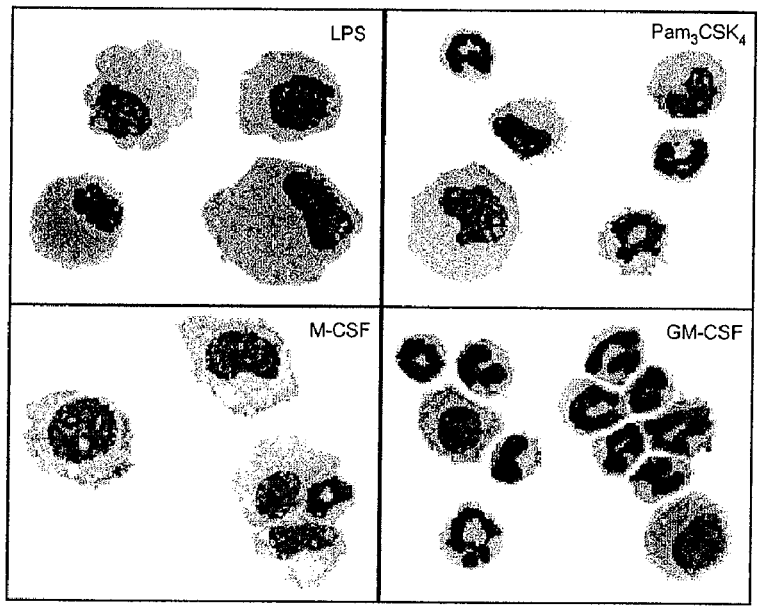
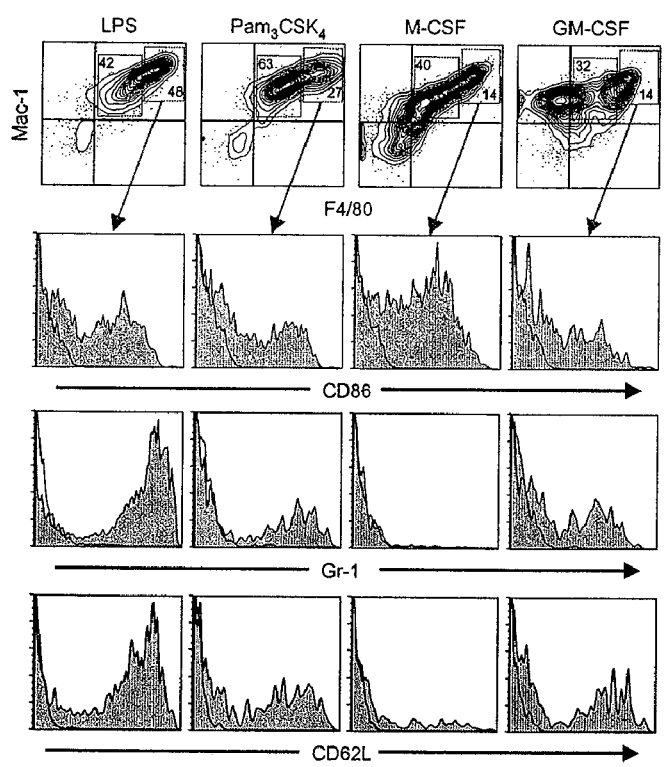
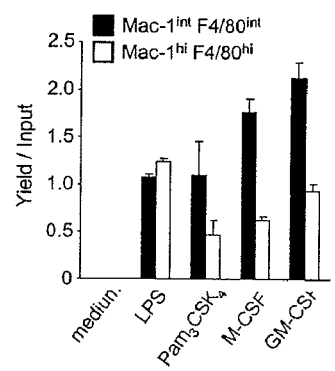
FIG. 5A-C

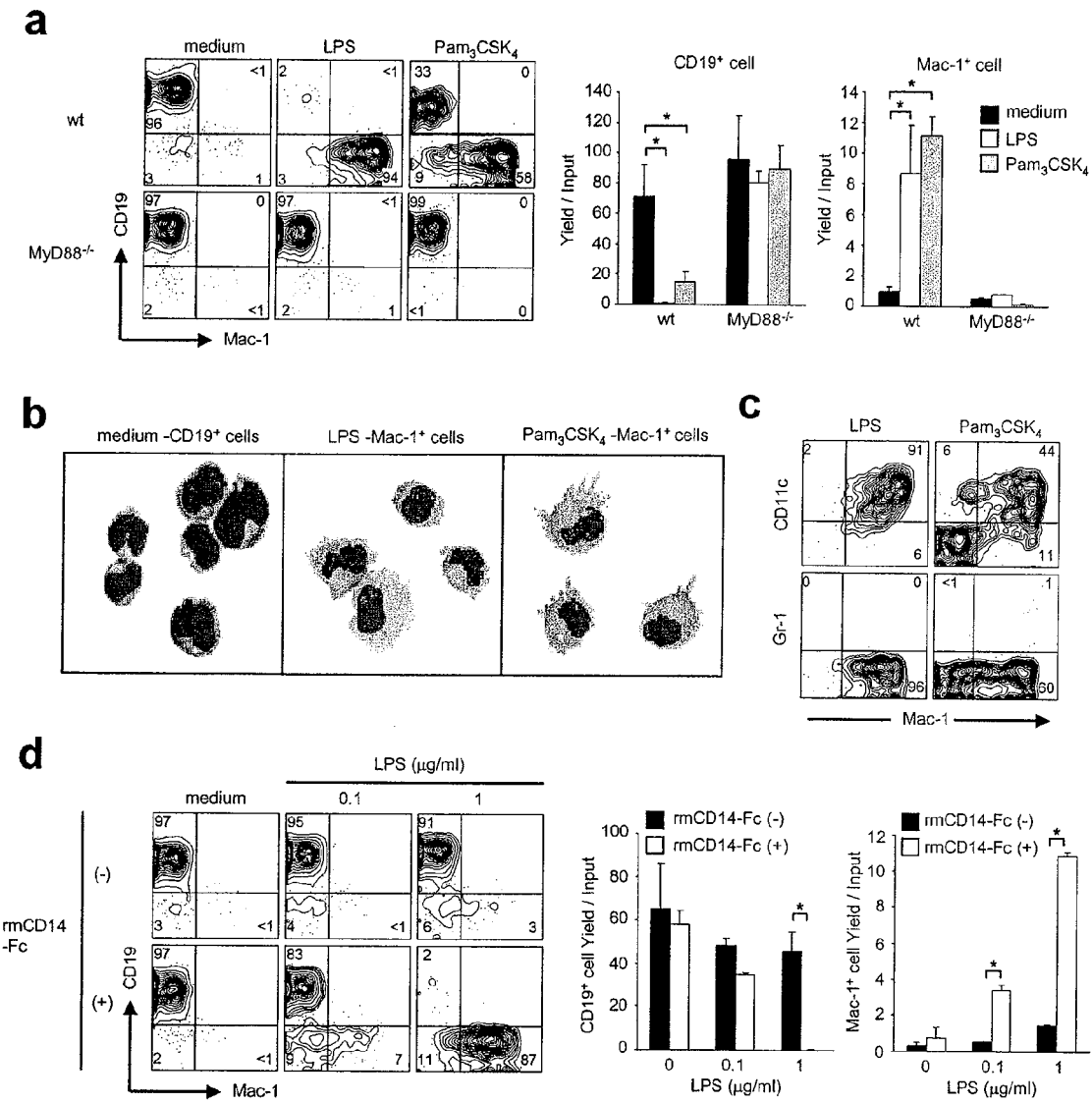
FIG. 6A-D

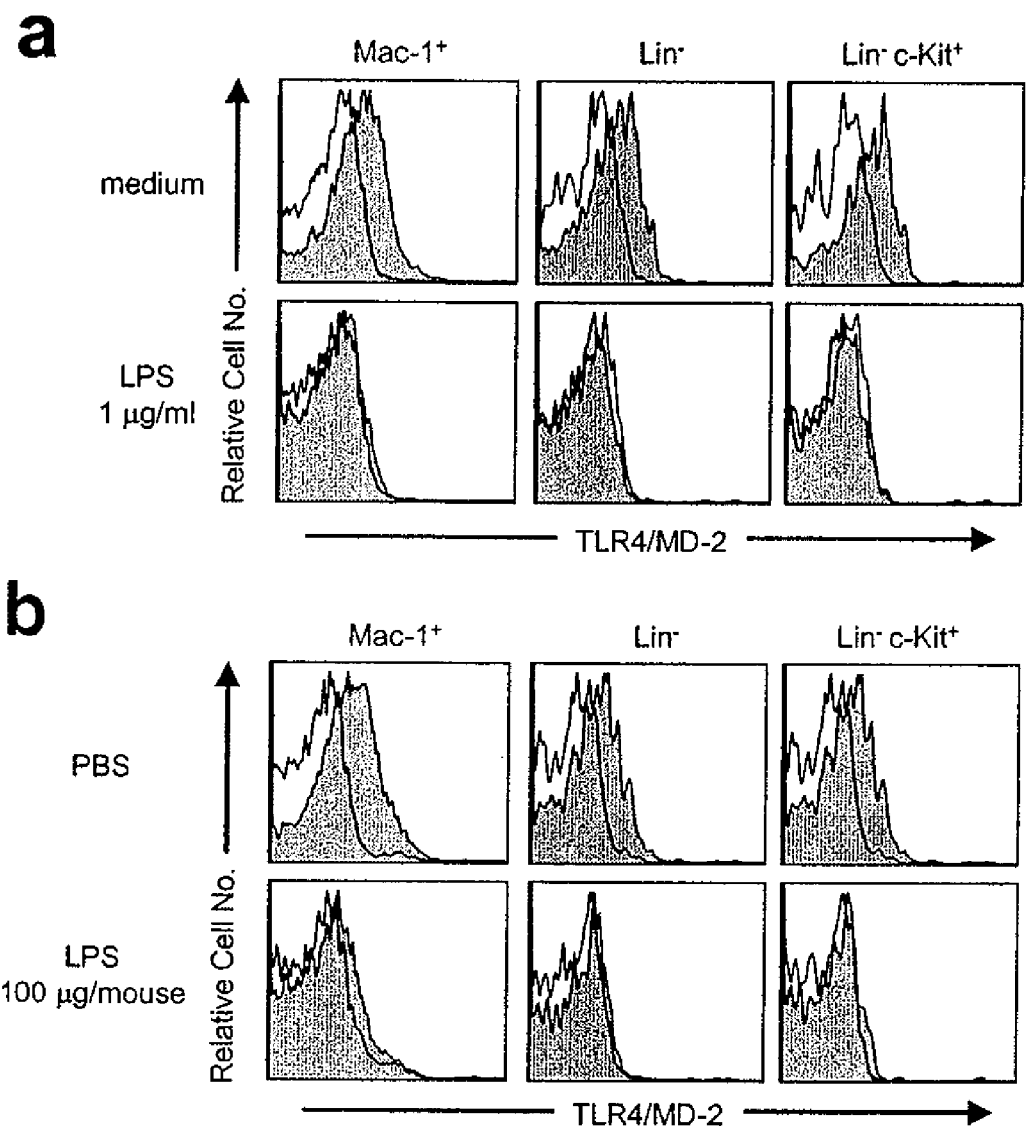
FIG. 8A-B

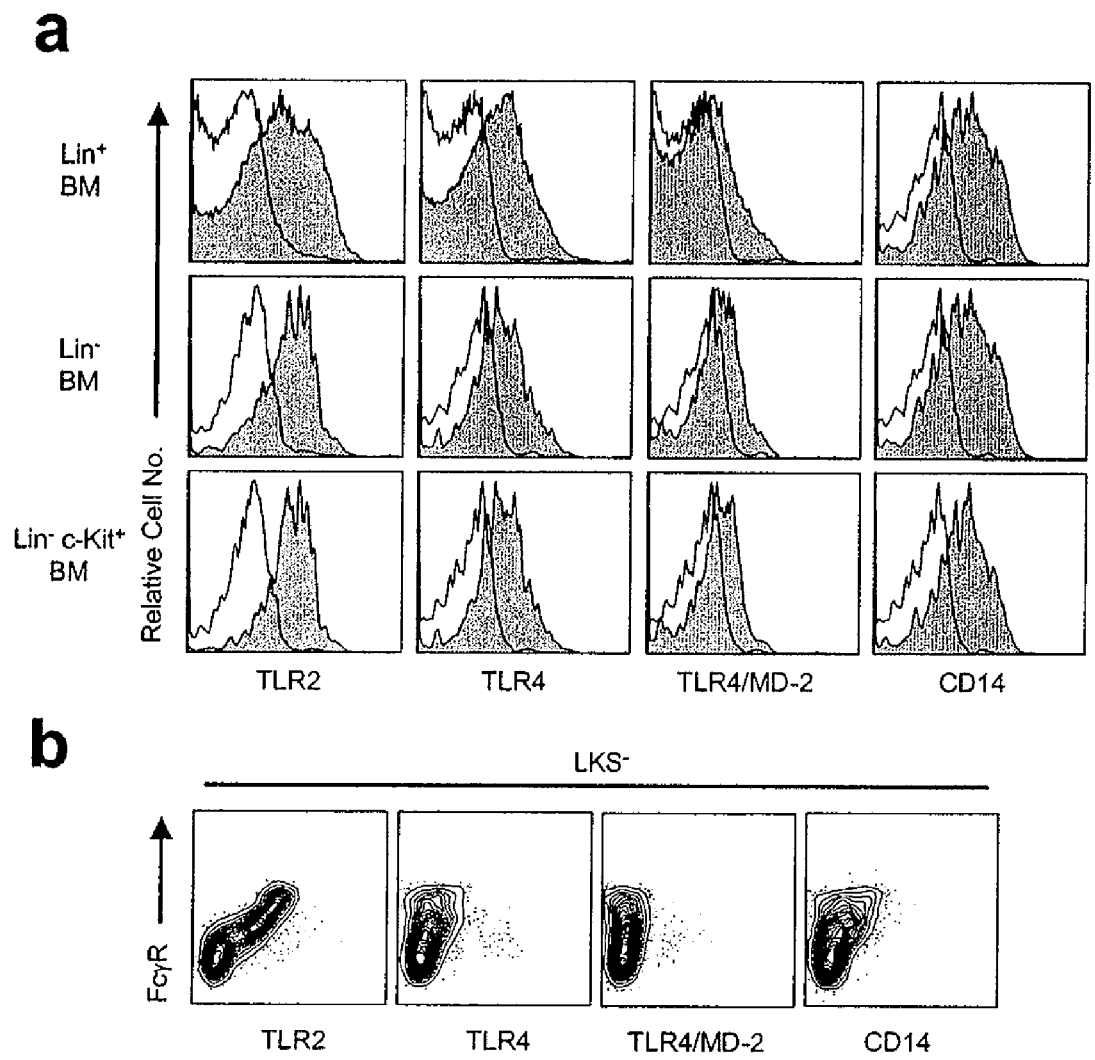
FIG. 9A-B

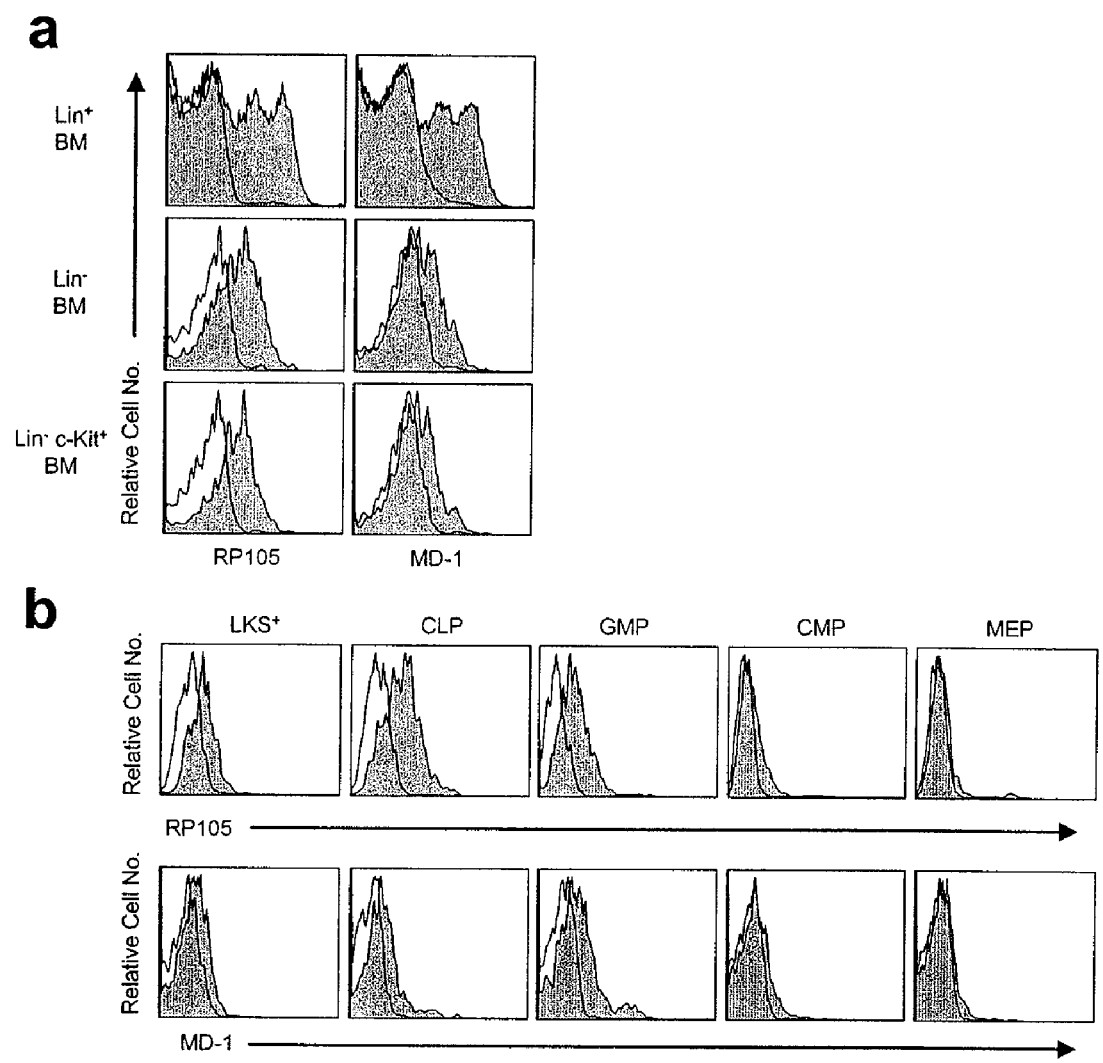
FIG. 10A-B

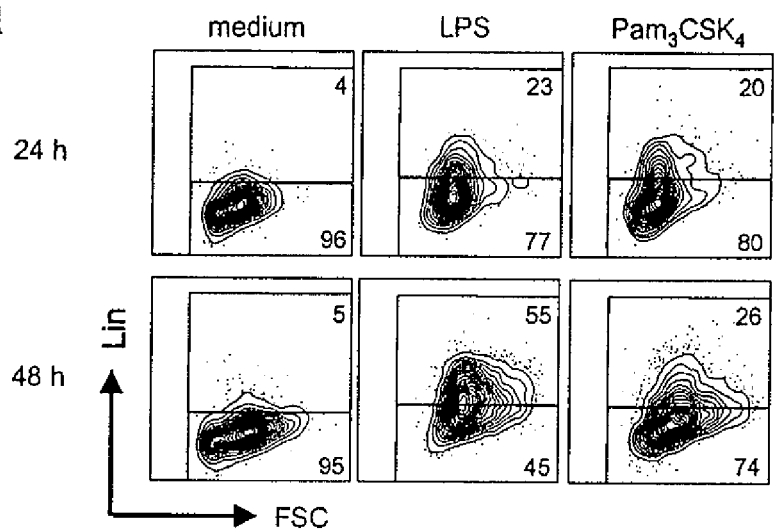
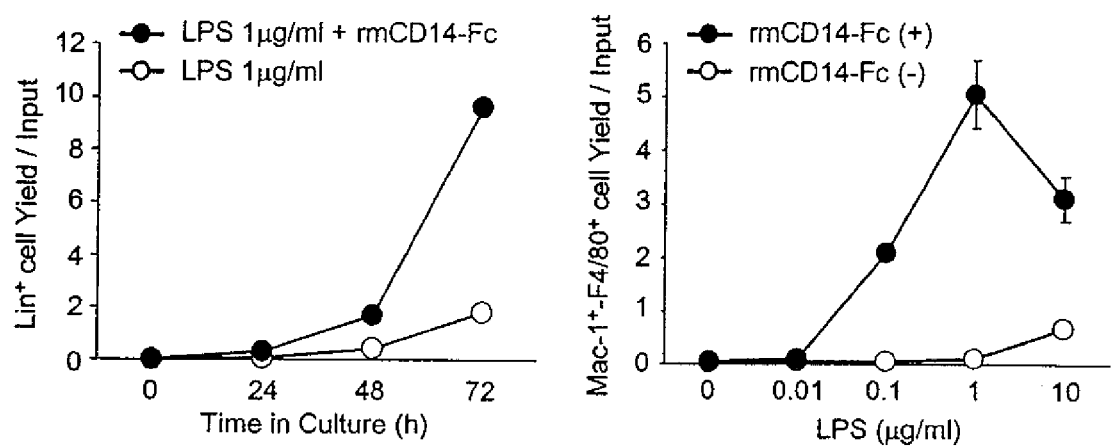
FIG. 11A-B

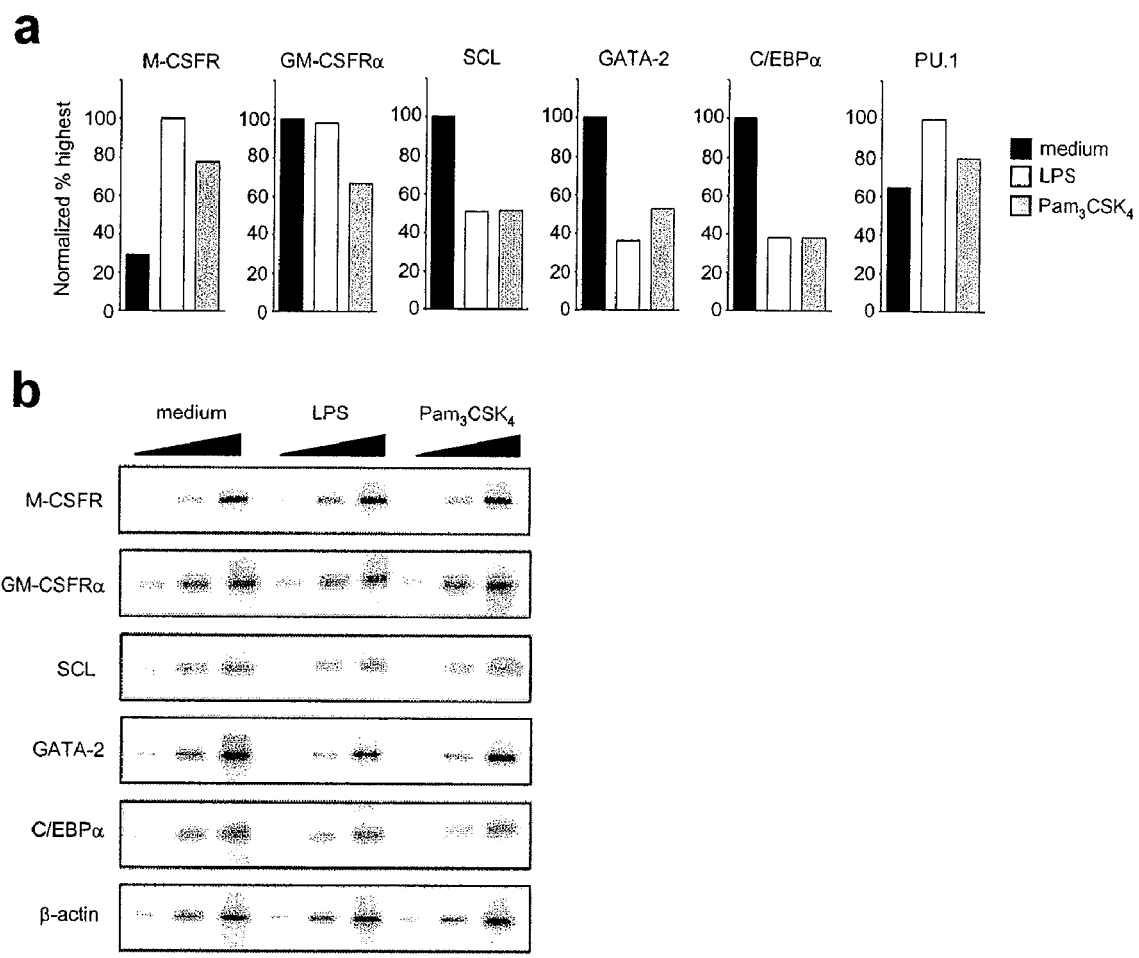
FIG. 12A-B

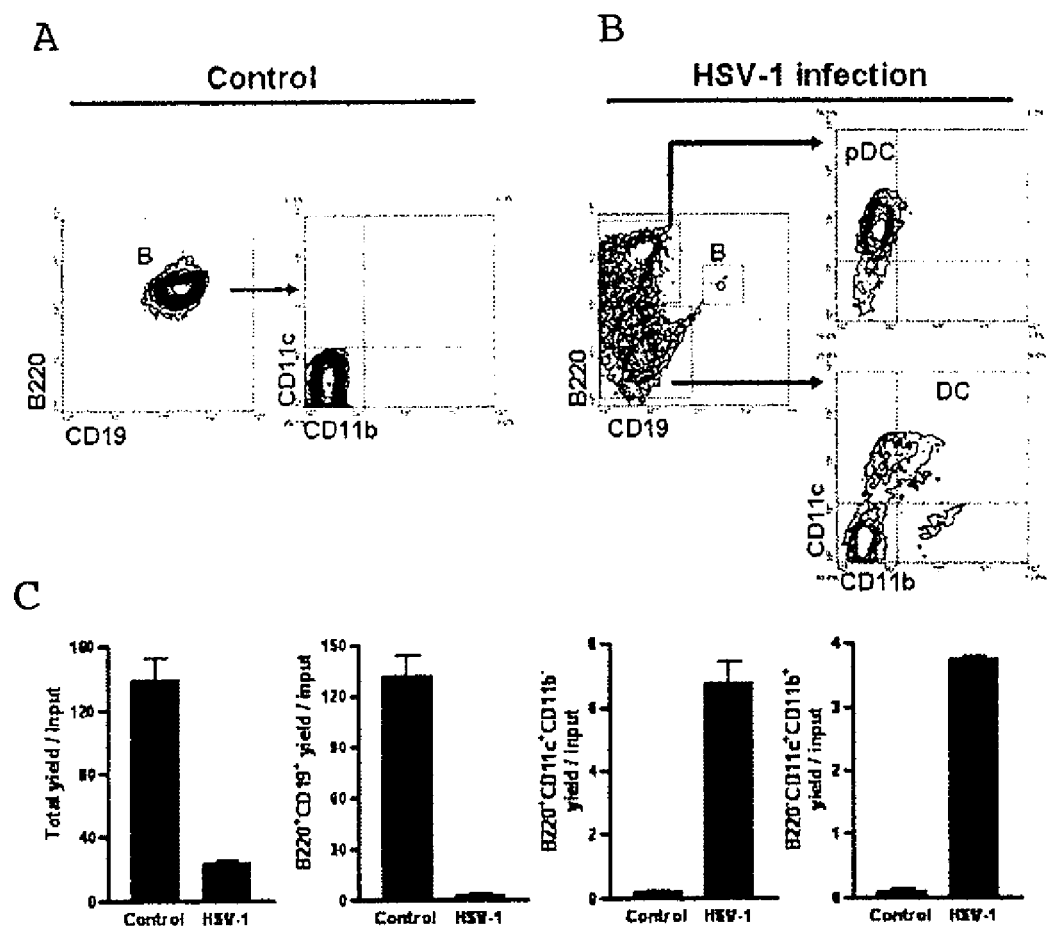
FIG. 17A-C

REGULATION OF TOLL-LIKE RECEPTORS ON STEM CELLS

The present invention claims benefit of priority to U.S. Provisional Applications Ser. No. 60/722,174, filed Sep. 30, 2005, and 60/806,351, filed Jun. 30, 2006, the entire contents of which are hereby incorporated by reference.

The invention was made with government support under grant numbers AI 20069 and AI 058162 awarded by the National Institutes of Health. The government has certain rights in the invention.

BACKGROUND OF THE INVENTION

1. Field of the Invention

The present invention relates generally to the fields of cell biology, developmental biology and immunology. More particularly, it concerns methods and compositions relating to the identification, stimulation and repression of stems cells that express Toll-like receptors.

2. Description of Related Art

Survival depends on an innate immune system that can quickly recognize and respond to microbial/viral products. The Toll-like receptors (TLRs) are responsible for much of that recognition and consequently have vital roles (Takeda et al., 2003). Activation via TLRs couples innate immunity with the adaptive immunity provided by lymphocytes (Iwasaki and Medzhitov, 2004). For example, TLR ligands induce dendritic cells (DCs) to mature and support the differentiation of T helper 1 (Th1) cells. Cells responsible for both innate and adaptive immunity have finite lifespans and must be constantly replenished from hematopoietic stem cells (HSCs) and progenitors in bone marrow (Kondo et al., 2003). Although TLRs on mature immune cells have been well studied, little is known about when maturing cells in bone marrow acquire functional TLRs and whether those receptors influence hematopoietic development.

HSCs give rise to a series of progenitors that gradually lose differentiation options and produce cells of a given type. For example, multipotent progenitors (MPP) spawn common myeloid progenitors (CMP) that give rise to either megakaryocyte/erythrocyte progenitors (MEP) or granulocyte/macrophage progenitors (GMP) (Akashi et al., 2000). Early lymphoid progenitors (ELP) capable of producing T, B and NK cells give rise to pro-lymphocytes/common lymphoid progenitors (CLP) that can then become pre-B cells (Igarashi et al., 2002; Kouro et al., 2002; Kondo et al., 1997). All information available to date indicates that commitment to, and progression within, these lineages requires well studied growth and differentiation factors such as colony stimulating factors. These and other extracellular cues control expression of key transcription factors such as EBF, C/EBPα and PU.1 (Henderson and Calame, 1998; Rosmarin et al., 2005).

There is considerable controversy concerning the plasticity of stem/progenitors, and many studies have described experimental circumstances where cells of one hematopoietic lineage gave rise to cells of a different kind (Kondo et al., 2000; Iwasaki-Arai et al., 2003; Iwasaki et al., 2003; Xie et al., 2004). However, this is generally believed to represent latent differentiation potential that would not be utilized under physiological conditions.

The TLR family recognizes well conserved microbial/viral components. For example, TLR4 recognizes bacterial lipopolysaccharide (LPS) from Gram-negative bacteria (Hoshino et al., 1999) while TLR2 recognizes peptidoglycan and lipoteichoic acid from Gram-positive bacteria (Takeuchi et al., 1999). Effective stimulation of cells via some TLRs requires cooperation with other molecules. The secreted MD-2 protein is associated with the extracellular portion of TLR4, and is essential for LPS recognition (Nagai et al., 2002). On B lymphocytes, the RP105/MD-1 complex cooperates with TLR2 and TLR4/MD-2 to cause antibody production to microbial membranes (Nagai et al., 2005). CD14 is known to cooperate with TLR2 and the TLR4/MD-2 complex in responses to lipoproteins and LPS respectively (Yoshimura et al., 1999; Means et al., 1999). In addition, TLRs require intracellular adaptor proteins for effective signaling. All TLRs except for TLR3 use the MyD88 adaptor protein for the production of inflammatory cytokines (Takeda and Akira, 2005). In addition, TLR3 and TLR4 use a MyD88-independent pathway, which is triggered by the TRIF/TICAM adaptor critical for induction of interferon-inducible genes (Yamamoto et al., 2003; Oshiumi et al., 2003).

A variety of defense mechanisms are triggered when microbial/viral products engage TLRs on innate immune cells. For example, TLR2/4 are linked to macrophage phagocytosis of bacteria (Blander and Medzhitov, 2004). TLR activation via MyD88 is required for phagosome maturation (Doyle et al., 2004). TLR signaling in DCs induces the expression of histocompatibility complex (MHC) and co-stimulatory molecules as well as the production of IL-12, a key cytokine for the induction of Th1 immune responses (Iwasaki and Medzhitov, 2004). In addition to these well-studied examples involving mature cells, there have been some hints that TLR might influence development within bone marrow. For example, chronic inflammation such as that elicited with endotoxin alters myeloid/lymphoid ratios in marrow (Ueda et al., 2004; Ueda et al,, 2005), and maturation of osteoclasts is altered by TLR ligands (Sato et al., 2004; Hayashi et al., 2003). Furthermore, Toll in *Drosophila* has a developmental role in determining dorso/ventral polarity and theoretically could contribute to other developmental processes (Ferrandon et al., 2004).

SUMMARY OF THE INVENTION

Thus, in accordance with the present invention, there is provided a method of stimulating a hematopoietic cell comprising (i) contacting the cell with a toll-like receptor (TLR) agonist; and (ii) culturing the cell. The TLR agonist may be a TLR ligand, an anti-TLR antibody, or a TLR ligand mimic. The hematopoietc cell may be a multipotent progenitor (MPP) cell, and the TLR agonist may be a TLR2 or TLR4 agonist, such as $Pam_3CSK_4$ or lipopolysaccharide. The stimulted MPP may differentiate into a monocyte/macrophage of the innate immune system. The MPP cell may also be contacted with a co-receptor component agonist, such as one directed at CD14 or MD-2. The MPP cell may be contacted with at least two TLR agonists, each directed to a distinct TLR. The method may further comprising contacting the stimulated MPP cell with a non-TLR cell growth or cell differentiation factor, and optionally include further culturing. The MPP cell may be isolated or characterized based on the profile $Lin^-IL-7R\alpha^-c-Kit^{hi}Sca-1^+Flk-2^+$.

The hematopoietic cell may be a common myeloid progenitor (CMP) cell, and the TLR agonist may be a TLR2 agonist, such as $Pam_3CSK_4$. The stimulated CMP cell may differentiate into a macrophage. The CMP cell may also be contacted with a co-receptor component agonist, such as one directed at CD14 or MD-2. The CMP cell may be contacted with at least two TLR agonists, each directed to a distinct TLR. The method may further comprise contacting the stimulated CMP cell with a non-TLR cell growth or cell differentiation factor, and optionally include further culturing. The CMP cell may be isolated or characterized based on the profile Lin$^-$IL-7Rα$^-$c-Kit$^{hi}$Sca-1$^-$ prior to step (i). The method may further comprise isolating the CMP cell based on CD34$^+$FcγR$^{lo}$.

The hematopoietic cell may be a granulocyte/macrophage progenitor (GMP), and the TLR agonist may be a TLR2 or TLR4 agonist, such as Pam$_3$CSK$_4$ or lipopolysaccharide. The stimulated cell may differentiate into a monocyte/macrophage of the innate immune system. The GMP cell may also be contacted with a co-receptor component agonist, such as one directed at CD14 or MD-2. The GMP cell may be contacted with at least two TLR agonists, each directed to a distinct TLR. The method may further comprise contacting the stimulated GMP cell with a non-TLR cell growth or cell differentiation factor, and optionally include further culturing. The GMP cell may be isolated or characterized based on the profile Lin$^-$IL-7Rα$^-$c-Kit$^{hi}$Sca-1$^-$CD34$^+$FcγR$^{hi}$.

The hematopoietic cell may be a common lymphoid progenitor (CLP). The TLR agonist may be a TLR2 or TLR4 agonist, such as Pam$_3$CSK$_4$ or lipopolysaccharide. The stimulated CLP cell may differentiate into a myeloid dendritic cell. The cell may also be contacted with a co-receptor component agonist, such as one directed at CD14 or MD-2. The CLP cell may be contacted with at least two TLR agonists, each directed to a distinct TLR. The method may further comprise contacting the stimulated CLP cell with a non-TLR cell growth or cell differentiation factor, and optionally include further culturing. The CLP cell may be isolated or characterized based on the profile Lin$^-$IL-7Rα$^+$c-Kit$^{lo}$Sca-1$^{lo}$.

The hematopoietic cell may be a hematopoietic stem cell (HSC), such as a long-term repopulating HSC (LTR-HSC). The TLR agonist may be a TLR2 or TLR4 agonist, such as Pam$_3$CSK$_4$ or is lipopolysaccharide. The stimulated HSC or LTR-HSC may be driven out of a quiescent state. The HSC cell may also be contacted with a co-receptor component agonist, such as one directed at CD14 or MD-2. The HSC may be contacted with at least two TLR agonists, each directed to a distinct TLR. The method may further comprise contacting a stimulated HSC with a non-TLR cell growth or cell differentiation factor, and optionally include culturing. The HSC may be isolated or characterized based on the profile Lin$^-$IL-7Rα$^-$c-Kit$^{hi}$Sca-1$^+$FLK-2$^-$.

In an additional embodiment, there is provided a method of isolating progenitor cells comprising (i) contacting a cell population with a toll-like receptor (TLR) ligand, wherein the TLR ligand is bound to a support; and (ii) isolating cells bound to the ligand. The method may further comprise enrichment by cell sorting. The ligand may be a TLR2 or TLR4 ligand, such as lipopolysaccharide, Pam$_3$CSK$_4$, an anti-TLR2 or -TLR4 antibody. The support may be a bead, a column matrix, a plate, a filter. The cell may be a GMP, a CMP, a CLP, an MMP, or an HSC. The progenitor cells may be 10-fold more pure, 50-fold more pure, 100-fold more pure or 1000-fold more pure than the cell population.

In yet an additional embodiment, there is provided a method for directing a lymphoid progenitor cell to become a myeloid dendritic cell comprising contact the progenitor cell with a toll-like receptor (TLR) agonist. The lymphoid progenitor cell may be obtained from a patient, treated ex vivo with the agonist, and returned to the patient. The TLR agonist may be a TLR2 or TLR4 agonist, such as an antibody to TLR2 or TLR4, Pam$_3$CSK$_4$ or lipopolysaccharide. The patient may be immunocompromised or immunodeficient, and may be a human.

In another embodiment, there is provided a method of protecting hematopoietic stem and primitive progenitor cells from response to ligation of toll-like receptor (TLR) comprising contacting said cells with a TLR pathway antagonist. The antagonist may be a soluble TLR, an anti-TLR antibody, or a soluble TLR dimerization mimic. The antagonist may be an siRNA, ribozyme, morpholino oligo, or an scFv or scAb. The antagonist may reduce MyD88 expression or function, such as a MAL/TIRAP antagonist. The antagonist may act on an MyD88-independent pathway, such as an antagonist that acts on TRAM or TRIF. The TLR pathway may be the TLR2, TLR4, or TLR9 pathway. The cells may also be contacted with a co-receptor component antagonist. The co-receptor component antagonist may be directed at CD14 or MD-2. Two distinct TLR pathways of said cells may be inhibited. The method may further comprise treating a patient in need of bone marrow or hematopoietic stem cell transplantation with said TLR pathway antagonist at the time of transplantation. The method may also further comprise treating said cells ex vivo prior to transplantation to a recipient patient. The method may also further comprise isolating said cells based on CD34$^+$ prior treating said cells with said TLR pathway antagonist.

In still yet another embodiment, there is provided a method for increasing the efficiency of lymphoid cell engraftment after transplantation into a patient comprising inhibiting one or more toll-like receptor (TLR) pathways of hematopoietic stem cells through contact with a TLR pathway antagonist. The cells may be obtained from said patient, treated ex vivo with said antagonist, and returned to said patient. The cell may be obtained from an allogeneic donor, treated ex vivo with said antagonist, and transplanted to said patient. The TLR pathway may be inhibited with a TLR2 or TLR4 antagonist. The antagonist may be a soluble TLR, an anti-TLR antibody, or a soluble TLR dimerization mimic. The antagonist may be an siRNA, ribozyme, morpholino oligo, or an scFv or scAb. The TLR pathway may be inhibited through inhibition of MyD88 expression or through inhibition of MyD88 function, such as a MAL/TIRAP antagonist. The antagonist may act on an MyD88-independent pathway, such as an antagonist that acts on TRAM or TRIF. The patient may be immunocompromised or immunodeficient, may be being treated with chemotherapy, and/or may undergone an organ transplant. The patient may be being or have been administered an immunosuppressant. The patient may suffer from an autoimmune disorder, or from another disorder or disease with an autoimmune component. The patient may be a human. The transplantation patient may be treated in vivo with said TLR pathway antagonist at the time of transplantation.

The hematopoietic cell may be a multipotent progenitor (MPP) cell, a common myeloid (CMP), a granulocyte/macrophage (GMP) cell, a common lymphoid progenitor (CLP) cell, or a hematopoietic stem cell (HSC). The MPP cell may be defined in the mouse as Lin$^-$IL-7Rα$^-$c-Kit$^{hi}$Sca-1$^+$Flk-2$^+$. The CMP cell in the mouse may be defined as Lin$^-$IL-7Rα$^-$c-Kit$^{hi}$Sca-1$^-$. The CMP cell in the mouse may also be defined as CD34$^+$FcγR$^{lo}$. The GMP cell in mice may also be defined as Lin$^-$IL-7Rα$^-$c-Kit$^{hi}$Sca-1$^-$CD34$^+$FcγR$^{hi}$. The CLP cell in mice may be defined as Lin$^-$IL-7Rα$^+$c-Kit$^{lo}$Sca-1$^{lo}$. The HSC cell may also be defined in the mouse as Lin$^-$IL-7Rα$^-$c-Kit$^{hi}$Sca-1$^+$FLK-2$^-$. Additional useful markers in the mouse are CD34 (absent on adult hematopoietic stem cells) and CD150 (present on HSC) (Yilmaz et al, 2006).

Hematopoietic tissues in human contain equivalent stem and progenitor cells that have been defined with a different collection of markers. For example, they lack CD13, CD14, CD33, CD64, glycophorin A, CD19, CD3, CD8 and CD56 associated with various blood cell lineages. Cell suspensions depleted of these lineage marker positive cells (Lin⁻) contain CD34⁺ CD38⁻ HSC. Also present are Lin⁻ CD34⁺ CD10⁺ lymphoid progenitors, Lin⁻ CD34⁺ CD38⁺ CD123/IL-3Rα$^{Lo}$ CD45RA⁻ CMP, Lin⁻ CD34⁺ CD38⁺ CD123/IL-3Rα$^{Lo}$ CD45RA⁺ GMP, and Lin⁻ CD34⁺ CD38⁺ CD123/IL-3Rα⁻ CD45RA⁻ MEP (Manz et al., 2002).

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-B—TLRs and related molecules are expressed by hematopoietic stem/progenitor cells. (FIG. 1A) Lineage marker negative cells were enriched from bone marrow suspensions before staining with antibodies to hematopoietic subsets and TLR2, TLR4, TLR4/MD-2, or CD14. Gating and flow cytometry analysis of LKS⁺, GMP, CMP, MEP, or CLP were as described by Kondo and colleagues (Konda et al., 2003). Open histograms depict staining with the appropriate isotype matched Abs. The results shown are representative of three independent experiments. (FIG. 1B) Total RNA was extracted from each progenitor subset and semi-quantitative RT-PCR was conducted to detect mRNA encoding TLR4, MD-2, TLR2, and CD14. The results are shown as values normalized to peak expression for each of the transcripts.

FIGS. 2A-D—Activation of TLRs through MyD88 on LKS⁺ cells leads to myeloid cell differentiation. (FIG. 2A) Left, sorted LKS⁺ cells (10,000 cells/well) from C57BL/6 or MyD88⁻/⁻ mice were cultured in the presence of FL and SCF with medium alone, LPS (10 μg/ml) or Pam₃CSK₄ (1 μg/ml). After 72 h in culture, cells were analyzed by flow cytometry for expression of lineage markers. Percentages indicate the frequencies of Lin⁺ or Lin⁻ cells. Right, the bar graph depicts yields, i.e., numbers of Lin⁺ cell recovered per input progenitor and the data represent mean values with standard deviations from triplicate cultures (*P<0.01). The results are representative of five independent experiments. (FIG. 2B) Expression of CD45R/B220 or myeloid cell markers (Mac-1 and/or Gr-1) on cultured cells. The bar graph depicts percentages of recovered cells bearing B220, CD11b/Mac-1 and/or Gr-1 lineage markers. Data represent mean values with standard deviations from triplicate cultures (*P<0.001). Similar results were obtained in three independent experiments. (FIG. 2C) Left, sorted LKS⁺ cells (10,000 cells/well) from C57BL/6 mice were cultured in the presence of FL and SCF with medium alone, LPS (10 μg/ml) or Pam₃CSK₄ (1 μg/ml). After 72 or 96 h in culture, cells were analyzed by flow cytometry for Mac-1 and F4/80. Right, the bar graph depicts cell yields. Data represent mean values with standard deviations from triplicate cultures and are representative of three independent experiments (*P<0.002). (FIG. 2D) Sorted LKS⁺ cells from C57BL/6 mice were cultured in the presence of FL and SCF with a range of concentrations of LPS (left, open circles), Pam₃CSK₄ (right, open circles) or a combination of mouse CD14-Fc protein (1 μg/ml) plus LPS (left, filled circles) or Pam₃CSK₄ (right, filled circles). After 72 h in culture, cells were analyzed by flow cytometry for expression of lineage markers. Data represent mean values with standard deviations from triplicate cultures (*P<0.001). The results are representative of three independent experiments.

FIGS. 3A-B—Stem cell rich Flk-2⁻ cells respond to TLR ligands and enter the cell cycle. (FIG. 3A) Left, sorted Flk-2⁻ or Flk-2⁺ LKS⁺ cells (10,000 cells/well) were cultured with medium alone, LPS (10 μg/ml) or Pam₃CSK₄ (1 μg/ml). Flk-2⁻LKS⁺ cells were cultured with SCF. Flk-2⁺LKS⁺ cells were cultured with SCF and FL. After 72 h in culture, cells were analyzed by flow cytometry for expression of lineage markers. Percentages given in quadrants indicate the frequencies of Lin⁺ or Lin⁻ cells and the bar graphs on the right depict cell yields. Data represent mean values with standard deviations from triplicate cultures and the results are representative of three independent experiments. (*P<0.03: Flk-2⁻ LKS⁺, *P<0.002: Flk-2⁺LKS⁺) (FIG. 3B) Sorted Flk-2⁻LKS⁺ (10,000 cells/well) were cultured in the presence of SCF with medium alone, LPS (10 μg/ml) or Pam₃CSK₄ (1 μg/ml) for 50 h, pulsing with 10 μM BrdU for the final 18 h. Cells were then stained with anti-BrdU. Percentages indicate the frequencies of BrdU⁺ cells and the results are representative of three independent experiments.

FIGS. 4A-D—Activation of TLRs through MyD88 bypasses normal differentiation cues and drives monocytes/macrophages differentiation of myeloid progenitors. (FIG. 4A) Sorted LKS⁻ cells from C57BL/6 or MyD88⁻/⁻ mice were stimulated with medium alone, LPS (10 μg/ml), Pam₃CSK₄ (1 μg/ml), M-CSF, or GM-CSF. After 72 h in culture, cells were analyzed by flow cytometry for expression of F4/80. Open histograms depict staining with the isotype matched Ab for F4/80. Percentages given in each histogram indicate the frequencies of F4/80⁺ cells and the results are representative of three independent experiments. (FIG. 4B) The bar graph depicts yields, i.e., numbers of F4/80⁺ cell recovered per input progenitor. Data represent mean values with standard deviations from triplicate cultures and the results are representative of three independent experiments (*P<0.005). (FIG. 4C) Sorted LKS⁻ cells from C57BL/6 mice were stimulated with LPS (10 μg/ml), Pam₃CSK₄ (1 μg/ml), M-CSF, or GM-CSF in the presence of anti-M-CSFR (10 μg/ml) or anti-GM-CSF (10 μg/ml). After 72 h in culture, cells were analyzed by flow cytometry for expression of F4/80. Data represent mean values with standard deviations from triplicate cultures and the results are representative of three independent experiments (*P<0.01). (FIG. 4D) Left, sorted CMP or GMP from C57BL/6 mice were stimulated with LPS (10 μg/ml) or Pam₃CSK₄ (1 μg/ml). After 24 or 48 h in culture, cells were analyzed by flow cytometry for expression of F4/80. Open histograms depict staining with the isotype matched Abs for F4/80. Frequencies of F4/80⁺ cells are given in each histogram and the bar graphs on the right depict cell yields. The data represent mean values with standard deviations from triplicate cultures and are representative of three independent experiments (*P<0.02).

FIGS. 5A-C—TLR stimulation drives differentiation of GMP into F4/80$^{hi}$ monocytes/macrophages. (FIG. 5A) These photomicrographs were prepared with Giemsa-May-Grünwald stained cytocentrifuged slides. (FIGS. 2B-C) Sorted GMP were stimulated with LPS (1 μg/ml), Pam$_3$CSK$_4$ (100 ng/ml), M-CSF, or GM-CSF. After 72 h in culture, cells were analyzed by flow cytometry for expression of F4/80 and Mac-1. Percentages indicate the frequencies of Mac-1$^{lo}$ F4/80$^{lo}$ or Mac-1$^{hi}$ F4/80$^{hi}$ cells. CD86, Gr-1, or CD62L were analyzed by flow cytometry on Mac-1$^{hi}$ F4/80$^{hi}$ cells. Open histograms depict staining with the appropriate isotype matched Abs. The results are representative of those obtained in two independent experiments. (FIG. 5C) The bar graphs depict cell yields of Mac-1$^{lo}$ F4/80$^{lo}$ or Mac-1$^{hi}$ F4/80$^{hi}$ cells. The data represent mean values with standard deviations from triplicate cultures and are representative of three independent experiments.

FIGS. 6A-D—TLR stimulation allows lymphoid biased progenitors to produce myeloid dendritic cells at the expense of B lymphopoiesis. (FIG. 6A) Sorted CLP (5,000/well) from C57BL/6 or MyD88$^{-/-}$ mice were stimulated in X-VIVO15 with medium alone, LPS (10 μg/ml) or Pam$_3$CSK$_4$ (100 ng/ml) plus SCF, FL and IL-7. After 7 days in culture, cells were analyzed by flow cytometry for expression of CD19 and Mac-1 (left). The bar graphs depict cell yields for CD19$^+$ cells or Mac-1$^+$ cells (right) and the data represent mean values with standard deviations from triplicate cultures (*P<0.02). The results are representative of those obtained in five independent experiments. (FIG. 6B) Subsets of the recovered cells described in FIG. 6A were sorted and used to prepare Giemsa stained slides. (FIG. 6C) Cultured cells from C57BL/6 mice were also analyzed by flow cytometry for expression of Gr-1 and CD11c. (FIG. 6D) Sorted CLP from C57BL/6 mice were cultured in the presence of SCF, FL and IL-7 with a range of concentrations of LPS or combination of recombinant mouse CD14-Fc protein (1 μg/ml) plus LPS. After 7 days in culture, cells were analyzed by flow cytometry for expression of CD19 and Mac-1 (left). The bar graph depicts cell yields for CD19$^+$ cells or Mac-1$^+$ cells (right). Data represent mean values with standard deviations from triplicate cultures (*P<0.003). The results are representative of three independent experiments.

FIGS. 8A-B LPS rapidly changes the TLR4/MD-2 complex on hematopoietic progenitors. (FIG. 8A) Whole bone marrow cells from C57BL/6 mice were cultured with medium alone or LPS (1 μg/ml) for 1 h. The cells were then harvested and stained with mAbs to TLR4/MD-2, Mac-1, lineage markers as described in Methods, and c-Kit. The MTS 10 reagent is unique in detecting a conformation dependent epitope on TLR4/MD-2 (Gilliet et al., 2002). Open histograms depict staining with the isotype matched Ab for TLR4/MD-2. The results are representative of three independent experiments. (FIG. 8B) C57BL/6 mice were intravenously or intraperitoneally injected with PBS or 100 μg LPS from E. coli. After 1 h, mice were sacrificed, and whole bone marrow cells were harvested and stained with mAbs to TLR4/MD-2, Mac-1, lineage markers, and c-Kit. Open histograms depict staining with the isotype matched Ab for TLR4/MD-2. The results are representative of three independent experiments.

FIGS. 9A-B—Lin$^-$ or Lin$^-$ c-Kit$^+$ progenitors in bone marrow express TLRs and related molecules, and the density of FcγR corresponds with TLR expression on myeloid/erythroid progenitors. (FIG. 9A) TLR2, TLR4, TLR4/MD-2, or CD14 were analyzed by flow cytometry on Lin$^+$, Lin$^-$ or Lin$^-$ c-Kit$^+$ bone marrow cells. Whole bone marrow cells from C57BL/6 mice were stained with mAbs to lineage markers as described in the Examples and c-Kit together with TLR2, TLR4, TLR4/MD-2, or CD14. Open histograms depict staining with the isotype matched Abs. The results shown are representative of two independent experiments. (FIG. 9B) Two color flow cytometry was used to evaluate FcγR2/3, TLR2, TLR4, TLR4/MD-2, and CD14 expression on LKS$^-$ cells. The results shown are representative of those obtained in two independent experiments.

FIGS. 10A-B—Lin$^-$ stem/progenitor cells express the RP105/MD-1 complex. (FIG. 10A) Expression of RP105 and MD-1 on gated populations of Lin$^+$, Lin$^-$ or Lin$^-$ c-Kit$^+$ bone marrow cells. Whole bone marrow cells from C57BL/6 mice were stained with mAbs to lineage markers and c-Kit together with RP105 or MD-1. Open histograms depict staining with the relevant isotype matched Abs and the results are representative of two independent experiments. (FIG. 10B) RP105 and MD-1 were analyzed on stem/progenitor cells in bone marrow using a different flow cytometer and background settings. Open histograms depict staining with the isotype matched Abs and the results are representative of two independent experiments.

FIG. 11A-B—TLR stimulation causes a progression of Lin$^+$ cells from LKS$^+$ cells and soluble CD14 augments the acquisition of Mac-1 and F4/80. (FIG. 11A) Sorted LKS$^+$ cells (10,000 cells/well) from C57BL/6 mice were cultured in the presence of FL and SCF with medium alone, LPS (10 μg/ml) or Pam$_3$CSK$_4$ (1 μg/ml). After 24 or 48 h in culture, cells were analyzed by flow cytometry for expression of lineage markers and percentages of Lin$^+$ or Lin$^-$ cells are indicated. (FIG. 11B) Left, sorted LKS$^+$ cells from C57BL/6 mice were cultured in the presence of FL and SCF with 1 μg/ml LPS (left, open circles) or a combination of recombinant mouse CD14-Fc protein (1 μg/ml) plus LPS (left, filled circles). After 24, 48, or 72 h in culture, cells were analyzed by flow cytometry for expression of lineage markers. The graph depicts cell yields and the results are representative of two independent experiments. Right, sorted LKS$^+$ cells from C57BL/6 mice were cultured in the presence of FL and SCF with a range of concentrations of LPS (right, open circles) or a combination of recombinant mouse CD14-Fc protein (1 μg/ml) plus LPS (right, filled circles). After 72 h in culture, cells were analyzed by flow cytometry for expression of Mac-1 and F4/80. The graph depicts cell yields and the data are representative of two independent experiments.

FIGS. 12A-B—TLR stimulation alters some lineage-associated gene patterns in Flk-2$^-$ HSCs. Sorted Flk-2$^-$ LKS$^+$ cells from C57BL/6 mice were stimulated with medium alone, LPS (10 μg/ml) or Pam$_3$CSK$_4$ (1 μg/ml) in the presence of SCF. After 24 h in culture, cells were harvested and mRNAs were isolated from cultured cells. Semi-quantitative RT-PCR was carried out to amplify transcripts for the indicated genes in each population. (FIG. 12A) The results are shown as values normalized to peak expression for each of the transcripts and actual bands are shown in (FIG. 12B).

(FIG. 14A) The results are shown as values normalized to peak expression for each of the transcripts and actual bands are shown in (FIG. 14B).

FIGS. 17A-C—Lymphoid biased progenitors in bone marrow of Herpes infected mice are re-directed to become dendritic cells. Bone marrow cells were harvested from mice 7 days after ocular infection with HSV-1. Lin− c-Kit$^{Lo}$ Sca-1+ IL-7Rα+ pro-lymphocytes/CLP were then sorted to high purity and tested for differentiation potential in serum-free, stromal cell-free cultures containing recombinant SCF, FL and IL-7. While pro-lymphocytes from control animals produced pure CD19+ lymphocytes (FIG. 17A), virtually none were present in cultures initiated with HSV-1 infected progenitors (FIG. 17B). Rather, there was dramatic production of CD45R/B220+ CD19− CD11c+ plasmacytoid dendritic cells, as well as CD45R/B220− CD19− CD11c+ CD11b+ myeloid dendritic cells. Actual yields of each of these cell types per input progenitor are shown in the bar graphs (FIG. 17C).

DESCRIPTION OF ILLUSTRATIVE EMBODIMENTS

Figure 7:
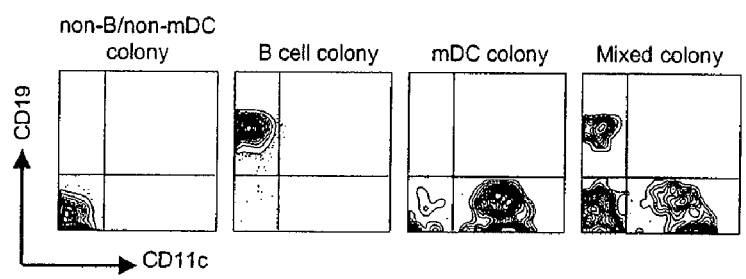
FIG. 7—Altered differentiation patterns of single lymphoid progenitors activated via TLRs. Sorted CLP were cultured in the presence of SCF, FL and IL-7 with medium alone, LPS (10 μg/ml) or Pam$_3$CSK$_4$ (1 μg/ml). After 24 h, cultured cells were harvested and washed three times with medium. Single cultured cells were then sorted and re-cultured on OP9 stromal cells in 96-well plates for 10 days in the presence of SCF, FL and IL-7. Positive colonies were examined by flow cytometry (representative examples shown on top row). The frequencies of wells with each of these differentiation patterns are shown along with total numbers of clones observed.

The principal goal of the present inventors here was to determine if TLRs are expressed on, and functional in, hematopoietic progenitor cells. Indeed, the inventors have now demonstrated that stem cell-enriched bone marrow fractions and some highly purified progenitor cells do display functional TLR2 and TLR4/MD-2. As on mature cells, the TLR4/MD-2 complex cooperates with CD14 at the cell surface. TLR signals on the progenitors require MyD88 for optimal responses to LPS and a synthetic lipopeptide. More surprising, however, was the finding that TLR ligation obviates some of the growth factors needed for differentiation of progenitors and drives them to become monocytes/macrophages. Additionally, lymphoid-biased progenitors were directed to a dendritic cell (DC) fate in response to TLR signals. Members of the TLR family may thus allow hematopoietic stem/progenitors to directly sense microbial/viral products, providing a means for boosting the innate immune system during infection.

The inventors envision exploiting these observations by utilizing the TLR signalling system on these cells to drive them out of a quiescent state, i.e. induce the cells out of the G0 phase of the cell cycle into active cell division, and into various differentiation patterns. For example, short-term repopulating hematopoietic stem cells can be induced to differentiate into innate immune cells. Common myeloid progenitor cells may similarly be induced to form macrophages, as can granulocyte/macrophage progenitors. Common lymphoid progenitor cells can be induced to form myeloid dendritics cells. Of particular interest are ligands for TLR2 (Pam$_3$CSK$_4$) and TLR4 (LPS).

In addition, antagonists for TLRs may prove useful in counteracting pro-inflammatory responses that can complicate systemic microbial infections, for keeping immune cells from being depleted in the face of chronic insult, and for preventing unwanted immune responses such as in autoimmunity. For this reason, the inventors sought to determine if inhibiting a TLR pathway would prevent a hematopoietic progenitor cell from differentiating into a mature component of the immune system, taking advantage of the observation that nearly all TLRs require the intracellular MyD88 adaptor protein for effective signaling. In engraftment experiments, bone marrow from MyD88 knockout mice produced more blood cells than bone marrow from mice with normal MyD88 function, indicating that the absence of TLR pathway signaling was preserving the blood-producing cells of the transplanted bone marrow from terminal differentiation. Rather that becoming components of the immune system, the MyD88-knockout cells continued to function as blood-producing stem cells.

The inventors thus propose inhibiting the TLR signaling pathways of hematopoietic progenitor cells in order to maintain the cells in a pluripotent state in the presence of TLR ligands, allowing the cells to continue producing immune system cells rather than becoming immune system cells. Temporary inhibition of TLR signalling in hematopoietic progenitor cells used for bone marrow transplants, for example, could thus lead to more rapid replenishment of the immune system. Small molecules, soluble TLRs or antibodies that interfere with the extracellular domains of the TLRs could also be employed, preventing interaction with intracellular signaling molecules before a natural ligand binds to TLR at the cell surface of effector cells. Also, the development of small molecules that interfere with the intracellular domains of the TLRs would prevent interaction with intracellular signaling molecules after ligand binding to TLRs. In addition, antagonists for TLRs may prove useful in counteracting pro-inflammatory responses that can complicate systemic microbial infections, for keeping immune cells from being depleted in the face of chronic insult, and for preventing non-beneficial immune responses such as in autoimmunity.

These, and other aspects of the invention, are set out in detail below.

I. Toll-Like Receptors

The innate immune system (macrophages, neutrophils, natural killer cells and the alternative complement pathway) is an early and rapid response system to microbial infection. The actions against the invading pathogens are either direct (e.g., phagocytosis and killing) or indirect through the release of cytokines or other stimulatory molecules, which trigger the adaptive immune system by activating B cells and T cells.

Janeway (1992) and Poltorak et al. (1998) proposed that the innate immune system identifies infectious agents by means of conserved structural features through pattern recognition receptors (PRRs). Microbial agents that trigger the immune response are termed pathogen-associated molecular patterns (PAMPs). The discovery of the Toll-like receptors (TLRs) provided the PRRs that detect these PAMPs.

TLRs are critical pattern recognition molecules that signal the presence of a microbial pathogen (Means et al,, 2000; Casadeval et al., 1999). These receptors are capable of recognizing highly conserved microbial constituents, and in so doing, they play a major role in host-pathogen interaction. Humans have one of the most active host immune responses to microbial antigens, but this heightened sensitivity makes humans more susceptible to bacterial toxins like lipopolysaccharide (LPS), more so than most any other mammalian species (Heurmann et al., 1998).

Toll was originally described in *Drosophila* as a type I transmembrane receptor that controls dorsal-ventral polarity during embryogenesis (Stein et al. 1991). The 018Wheeler (18W) protein is a homolog of *Drosophila* Toll. Toll and 18W share the greatest similarity to each other, as well as to the cytoplasmic tail of the mammalian IL-1R1. The extracellular regions of Toll and 18W contain multiple leucine-rich repeats and carboxyl-terminal cysteine-rich domains (Eldon 1994)).

The TLRs of different species are very different: mouse TLR4 and human TLR4 are only 53% identical. Genetic studies of leucine-rich repeat structures among different individuals also revealed that polymorphisms are responsible for a different reaction on microbial challenge. The intracellular part contains a cytoplasmic domain of approximately 200 amino acids that is evolutionarily conserved. This highly conserved region is known as the TIR domain (O'Neill et al., 2000).

The mammalian homologs of *Drosophila* Toll are known as TLRs. To date, ten human TLRs have been described (Medzhitov et al., 1997; Chaudhary et al., 1998; Takeuchi et al., 1999; Du et al., 2000). TLR1-TLR6 have been characterized by their distinctive expression patterns with mRNA detection assays. TLR1 is expressed ubiquitously and at rather high levels. TLR2 have been known to be expressed in peripheral blood mononuclear cells, as well as in lymphoid tissue (Yang et al., 1999). TLR3 is expressed in lung, muscle, heart, brain and intestinal cells, with alternative splicing reported in pancreas and placenta. Among peripheral blood cells, TLR3 is selectively expressed in specific subsets of dendritic cells (Kadowaki et al., 2001). TLR4 was known to be expressed by monocytes/macrophages, dendritic cells, lymphocytes, the spleen and the heart. TLR5 mRNA is found in peripheral blood monocytes, leukocytes, the ovary and the prostate. TLR6 expression is found in the spleen, the thymus, the ovary and the lung (Takeuchi et al., 1999). TLR mRNA is also expressed in various epithelial cells (Cario et al., 2000), suggesting a role in monitoring for invading microbes.

A. Functional Roles

TLR2 and TLR4. TLR2 and TLR4 are the most extensively studied members of mammalian homologs to *Drosophila* Toll. Both TLR2 and TLR4 require the adapter protein MyD88 for signaling, and immunoprecipitation studies showed direct interaction of MyD88 and IRAK (Medzhitov et al., 1998). MyD88 was originally isolated and characterized as a myeloid differentiation primary response gene. MyD88 itself consists of a carboxyl-terminal TIR domain. IRAK has been shown both to interact with both MyD88 and TRAF6 (Chaudhary et al., 1998).

Research has demonstrated the necessity of another cell surface molecule for TLR4 signal transduction (Shimazu et al., 1999). The protein MD-2 has no intracellular domain, but on co-expression with TLR4 enhances LPS sensitivity in transfection models. MD-2 cotransfection with TLR2 had no effect on LPS response. Data support a direct binding of MD-2 to LPS. This effect was independent of CD14 or LPS-binding protein (LBP) and suggests a specific and unique role for MD-2 in LPS recognition that contributes to modulation of the proinflammatory response of effector cells (Viriyakosol et al., 2001).

TLR2 forms heterodimeric structures with other TLR members such as TLR1 and TLR6. A recent report demonstrated that the p85 regulatory subunit of phosphatidylinositol-3'-kinase can directly associate with the intracellular domain of TLR2 (Arbibe et al., 2000), and the Rho-type GTPase Rac1 also appears to be associated with TLR2-mediated signaling. This alternative pathway activates a number of phosphorylated lipids, resulting in the generation of the intracellular protein kinase Akt. This pathway directly activates NF-κB, independent of the phosphorylation and degradation of I-κB (Arbibe et al., 2000).

TLR4 is utilized by LPS and therefore is the long-sought LPS receptor (Poltorak et al., 1998; Qureshi et al., 1999). LPS has been known to induce signals very similar to IL-1, and also to bind to CD14 on macrophages. CD14 is a known PRR on the surface of monocytes/macrophages. It has been clear for many years that CD14 has a major role for the effects of LPS on macrophages, monocytes, and neutrophils, and that CD14 increases the sensitivity of macrophages to LPS (Schröder et al., 2000). TLR4 induces the expression of the NF-κB-controlled cytokines IL-1, IL-6 and IL-8, implicating a role for this receptor in innate immunity (Medzhitov et al., 1997). Others then proved on a genetic level that TLR4 was involved in LPS signaling (Poltorak et al., 1998).

RP105. RP105 was placed in the TLR family on the basis of sequence homology, and shown to form a complex with MD-1. This complex is preferentially expressed by B lineage lymphocytes, dendritic cells and macrophages (Kimoto et al., 2003). On B lymphocytes, the RP105/MD-1 complex cooperates with TLR2 and TLR4/MD-2 to cause antibody production to microbial membranes (Nagai et al., 2005). However, the RP105/MD-1 complex can be a negative regulator of TLR4 signaling on macrophages (Divanovic et al., 2005).

TLR9. Another member of the mammalian TLR family is TLR9. Hemmi et al. (2000) first defined the TLR9 molecule as the receptor for bacterial DNA. Abundant mRNA transcripts of TLR9 were found in many tissues, suggesting a physiological role, which was confirmed by the generation of a TLR9−/− knockout mouse strain. These animals were shown to be incapable of responding to unmethylated CpG motifs of synthetic oligonucleotides.

Bacterial DNA has been known as a potent immunostimulant for mammalian cells for years. Unmethylated CpG motifs are found in microbial DNA, while these sequences are relatively rare in human DNA. When these unmethylated CpG sequences are flanked by two purines on the 5' side and two pyrimidines on the 3' end of the immunostimulatory nucleic acid, sequences in bacterial DNA induce a strong proinflammatory signal for human immune effector cells (Krieg, 1999). The specific sequences that are optimally recognized by human cells are GT-C-p-G-TT, while murine cells recognize GA-C-p-G-TT (Bauer et al., 2001).

The molecular basis for discrimination between bacterial and human DNA remained obscure until the observations that TLR9-DN mutants had no TNF, IL-12, IL-6 and interferon-γ response on exposure to oligonucleotides containing microbial CpG motifs (Hemmi et al., 2000). TLR9 knockout mice also are refractory to lethal shock from synthetic oligonucleotides bearing unmethylated CpG motifs that normally induce rapid hypotension and lethality in wild-type mice.

Evidence indicates that TLR9 is expressed on in the endomsome of immune effector cells. Interestingly, oligonucleotides immobilized on solid surfaces fail to stimulate mammalian cells, while inhibitors of cellular uptake disrupt signaling by CpG DNA. This indicates that prokaryotic DNA may need to be internalized within the endosomal compartment before initiation of the specific signaling cascade. MyD88 colocalizes with tagged TLR9 at the endosomal compartment (Hemmi et al., 2000).

TLR5. The major ligand for TLR5 is bacterial flagellin from either Gram-positive or Gram-negative bacteria. These proteins are highly conserved among bacterial pathogens, and considerable structural homology is essential to maintain the integrity of the locomotion system of bacterial organisms. Isolated and purified flagella protein itself, or flagellin proteins expressed on the cell surface of either Gram-positive or Gram-negative bacteria, stimulate monocyte/macrophage cells in a TLR5-specific, CD14-independent manner. The TLR5 receptor thus appears to be the main route through which the immune system recognizes flagellated bacteria (Hayashi et al., 2001).

B. Ligands

TLR2 has been recognized as a signal transducer for numerous bacterial products. TLR2 ligands include lipoteichoic acid, synthetic lipopeptides ($Pam_3CSK_4$, MALP-2) and the yeast-derived Zymosan. TLR4 signaling is primarily activated after lipid A/LPS challenge. Purified glycolipids from *Treponema brennaborense*, a spirochete that causes a bovine infectious disease, have been associated with TLR4-dependent signaling.

Ohashi et al. reported the potential first endogenous ligand for the TLR4 (Ohashi et al, 2000) Viral particles also act as a ligand for TLR4. Kurt-Jones et al. (2000) showed that the innate immune response to respiratory syncytial virus coat protein F is mediated by signaling through TLR4 and CD14. Respiratory syncytial virus infection persisted longer in the lungs of TLR4-deficient mice compared with normal mice (Haynes et al., 2001).

The TLR3 ligand polyinosine-polycytidylic acid (poly(I:C)) is a synthetic analog of double-stranded RNA (dsRNA), a molecular pattern associated with viral infection. dsRNA is known to induce the activation of NF-κB and the production of interferon-β through distinct mechanisms that are MyD88-dependent or MyD88-independent.

TLR4 signaling is primarily activated after lipid A/LPS challenge. Purified glycolipids from *Treponema brennaborense*, a spirochete that causes a bovine infectious disease, have been associated with TLR4-dependent signaling. Ohashi et al. reported the potential first endogenous ligand for the TLR4 (Ohashi et al., 2000) Other endogenous ligands include heat shock protein gp96 (Liu et al., 2003). Viral particles also act as a ligand for TLR4. Kurt-Jones et al. (2000) showed that the innate immune response to respiratory syncytial virus coat protein F is mediated by signaling through TLR4 and CD14. Respiratory syncytial virus infection persisted longer in the lungs of TLR4-deficient mice compared with normal mice (Haynes et al., 2001).

The TLR5 ligand flagellin is the major component of the bacterial flagellar filament, which confers motility on a wide range of bacterial species. Flagellin is a potent stimulator of innate immune responses in a number of eukaryotic cells and organisms, including both mammals and plants. In mammals, flagellin triggers defense TLR5-dependent responses both systemically and at epithelial surfaces. Flagellin induces the activation of NF-κB and the production of cytokines and nitric oxide depending on the nature of the TLR5 signaling complex.

TLRs 7 and 8 were initially discovered as being responsive to nucleoside analogs, but more recently, the natural ligands were found to be ssRNA. Imiquimod (R837), an imidazoquinoline amine analogue to guanosine, is an immune response modifier with potent indirect antiviral activity. This low molecular synthetic molecule induces the production of cytokines such as IFN-α. Unlike R848, Imiquimod activates only TLR7 but not TLR8. Loxoribine is a guanosine analog derivatized at position N7 and C8. This L-nucleoside is a strong stimulator of the immune system but until recently the mechanisms responsible for this immunostimulatory activity was unknown. It appears that similar to imidazoquinolines, a family of small synthetic antiviral molecules that includes imiquimod, loxoribine activates the innate immune system through TLR7. Similar to imiquimod, loxoribine recognition is restricted to TLR7. This activation is MyD88-dependent and leads to the induction of the transcription factor NF-κB.

TLR9 is activated by specific unmethylated CpG-containing sequences in bacterial DNA or synthetic oligonucleotides (ODNs) in the endosomal compartment. These specific sequences called CpG motifs are present at high frequency in bacterial DNA but rare in mammalian DNA. The methylation status is a crucial distinction between bacterial and mammalian DNA. Unmethylated ODNs including a CpG motif can mimic the effects of bacterial DNA, inducing B-cell proliferation and activating cells of the myeloid lineage.

II. Toll-like Receptor Pathways

A. MyD88

Mammalian MyD88 is an adapter protein in the signal transduction pathway mediated by interleukin-1 (IL-1) and Toll-like receptors. In *Drosophila*, the Toll pathway was originally characterized for its role in the dorsoventral patterning of the embryo. Like Toll, *Drosophila* Myd88 messenger RNA is maternally supplied to the embryo. Homozygous mutant Myd88 female flies lay dorsalized embryos that are rescued by expression of a transgenic Myd88 complementary DNA. The *Drosophila* Myd88 mutation blocks the ventralizing activity of a gain-of-function Toll mutation. These results show that *Drosophila* Myd88 encodes an essential component of the Toll pathway in dorsoventral pattern formation (Kambris, 2003).

A second study also established a role for Myd88 in dorsoventral patterning. Myd88 was revealed by a mutation in krapfen (kra) in a genetic screen for new maternal genes involved in embryonic pattern formation. The embryos laid by homozygous $kra^{56}$ females fail to gastrulate properly and die as hollow tubes of dorsal cuticle. This phenotype is undistinguishable from those caused by mutations in the dorsal group of genes. Epistasis experiments have revealed that krapfen acts between Toll and Tube. A direct interaction was detected in yeast two hybrid experiments between Krapfen and Tube, presumably mediated by the death domains present in both proteins. Tube in turn interacts with its downstream effector Pelle through death domain association. It is therefore suggested that upon Toll activation, Myd88 associates with Pelle and Tube, in an heterotrimeric complex (Charatsi, 2002).

The Toll pathway was identified in *Drosophila* on the basis of its role in dorsoventral patterning during early embryogenesis. Genetic screens have led to the identification of maternal effect genes involved in the generation, transmission and interpretation of the signals specifying dorsoventral polarity in the embryo. Loss-of-function mutations in 11 of these genes result in a common maternal-effect lethal phenotype: fertilized eggs laid by homozygous mutant females produce embryos in which all cells adopt the cell fate normally restricted to the cells on the dorsal surface of the embryo, thus resulting in hollow tubes of dorsal cuticle. Loss-of-function mutations in the twelfth gene, cactus, result in the opposite (ventralized) phenotype. Genetic and molecular studies are consistent with a model in which a proteolytic cascade activated on the ventral side of the embryo generates an active ligand for the transmembrane receptor Toll. Activated Toll triggers phosphorylation and degradation of the inhibitor Cactus that releases the Rel transcription factor Dorsal, allowing its nuclear translocation. In the nucleus, Dorsal directs the expression of ventral-specific genes, such as twist, and represses dorsal-specific ones. Signal transduction from Toll to Cactus requires the proteins Tube and Pelle. These two proteins co-localize at the plasma membrane and interact through their death domains. Pelle is a serine/threonine kinase that can phosphorylate itself, and also Tube and Toll. How Pelle signals to Cactus is still unknown (Kambris, 2003).

Components of this pathway between the putative Toll ligand Spätzle and Cactus also have a major role in *Drosophila* adults in the control of fungal and Gram-positive bacterial infections. The output of this pathway in adults is the nuclear translocation of the Rel protein Dorsal-related immunity factor (Dif), that upregulates the transcription of antimicrobial peptide genes such as *drosomycin*. The discovery of the critical role of Toll in innate immunity in flies led to the identification of homologous genes in mammals that have been called Toll-like receptors (TLRs) and which have been shown to be required for the recognition of microbial ligands. TLRs and receptors of the interleukin-1 (IL-1) family interact with the protein MyD88 to activate the Rel transcription factor NF-kappaB, and MyD88 interacts with the Pelle-related kinases of the IRAK family. These interactions are mediated by homophilic associations involving two well-defined structural domains of MyD88: the carboxy-terminal Toll/IL-1 receptor (TIR) domain interacts with the cognate domains in the intracytoplasmic tails of the TLRs, and the amino-terminal death domain mediates interaction with the corresponding domain of IRAK. Sequencing of the *Drosophila* genome led to the identification of a molecule related to MyD88 that interacts physically with Toll and with the kinase Pelle, and that functions upstream of Tube and Pelle (Horng, 2001; Sun, 2002; Tauszig-Delamasure, 2002). *Drosophila* Myd88 differs from its mammalian counterpart by the presence of a 162 amino-acid C-terminal extension following the TIR domain that is encoded by a separate exon. Flies carrying a transposon inserted at the 5' end of this gene have an impaired response to infection (Tauszig-Delamasure, 2002). Another mutant allele of Myd88 has been identified that encodes a protein devoid of its C-terminal extension. Analysis of these mutant flies reveals that Myd88 encodes a component of the dorsoventral pathway in *Drosophila* embryos (Kambris, 2003).

Signaling via TLR2 and TLR4 requires the TIR-domain-containing adaptor protein (TIRAP), also called MyD88 adaptor-like (Mal). TIRAP functions as a "sorting adaptor" to recruit the signaling adaptor MyD88 to the membrane (Fitzgerald & Chen, 2006).

B. MyD88-Independent Signaling

At least two Toll-like receptors, TLR3 and TLR4 can transmit signals for biological responses without utilization of the MyD88 adaptor protein. These are thought to be mediated by TRIF and in some cases TRAM, resulting in interferon production (O'Neill, 2005). While it is already clear that hematopoietic stem and progenitors utilize the MyD88 adaptor protein, the alternative pathways may also be important. Thus, agonists and antagonists to these molecules may be used alone or in conjunction with MdD88 pathway inhibitors for therapeutic applications.

III. Detection of Cell Surface Markers

A. Antibody Constructs

Antibodies directed against the various cell surface antigens are readily available from commercial sources. While available from commercial sources, it is also contemplated that monoclonal or polyclonal antibodies for use in the context of the invention may be constructed by a person of ordinary skill.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art. Means for preparing and characterizing antibodies are also well known in the art (see, e.g., Antibodies: A Laboratory Manual, Cold Spring Harbor Laboratory, 1988; incorporated herein by reference).

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

The methods for generating monoclonal antibodies (MAbs) generally begin along the same lines as those for preparing polyclonal antibodies. Briefly, a polyclonal antibody is prepared by immunizing an animal with a LEE or CEE composition in accordance with the present invention and collecting antisera from that immunized animal.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, toxins, plasmodia, synthetic compositions or LEEs or CEEs encoding such adjuvants.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary, often preferred adjuvants include complete Freund's adjuvant (a non-specific stimulator of the immune response containing killed *Mycobacterium* tuberculosis), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, cimetidine (CIM; 1200 mg/d) (Smith/Kline, PA); low-dose cyclophosphamide (CYP; 300 mg/m2) (Johnson/Mead, NJ), cytokines such as γ-interferon, IL-2, or IL-12 or genes encoding proteins involved in immune helper functions, such as B7 (CD80).

The amount of immunogen composition used in the production of polyclonal antibodies varies upon the nature of the immunogen as well as the animal used for immunization. A variety of routes can be used to administer the immunogen including but not limited to subcutaneous, intramuscular, intradermal, intraepidermal, intravenous and intraperitoneal. The production of polyclonal antibodies may be monitored by sampling blood of the immunized animal at various points following immunization.

A second, booster dose (e.g., provided in an injection), may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

MAbs may be readily prepared through use of well-known techniques, such as those exemplified in U.S. Pat. No. 4,196, 265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60-61), but mice are preferred, with the BALB/c mouse being most preferred as this is most routinely used and generally gives a higher percentage of stable fusions.

The animals are injected with antigen, generally as described above. The antigen may be mixed with adjuvant, such as Freund's complete or incomplete adjuvant. Booster administrations with the same antigen or DNA encoding the antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, X63-Ag8.653, NS1/1.Ag 41, Sp210-Ag14, FO, NSO/U, MPC-11, MPC-11-X45-GTG1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding, 1986).

Fusion procedures usually produce viable hybrids at low frequencies, about 1×10-6 to 1×10-8. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies. In another example, LEEs or CEEs can be used to produce antigens in vitro with a cell free system. These can be used as targets for scanning single chain antibody libraries. This would enable many different antibodies to be identified very quickly without the use of animals.

Alternatively, monoclonal antibody fragments encompassed by the present invention can be synthesized using an automated peptide synthesizer, or by expression of full-length gene or of gene fragments in E. coli.

B. Antibody Conjugates

The instant invention provides for the use of antibodies against various target antigens, including TLRs, which are generally of the monoclonal type, and that may be linked to at least one agent to form an antibody conjugate. It is conventional to link or covalently bind or complex at least one desired molecule or moiety. Such a molecule or moiety may be, but is not limited to a reporter molecule. A reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Any antibody of sufficient selectivity, specificity or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al., 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al., 1988), and contains epitopes (idiotopes) recognized by anti-antibodies (Kohler et al., 1989).

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired.

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might employ, by way of example, ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might employ, for example, $^{211}$astatine, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, $^{99m}$technicium and/or $^{90}$yttrium. $^{125}$I is often being preferred for use in certain embodiments, and $^{99m}$technicium and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugate contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

C. Methods of Conjugation

If desired, the compound of interest may be joined to an antibody via a biologically-releasable bond, such as a selectively-cleavable linker or amino acid sequence. Certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the moiety prior to binding at the site of action.

Additionally, any other linking/coupling agents and/or mechanisms known to those of skill in the art can be used to combine to components or agents with antibodies of the present invention, such as, for example, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, or combinations thereof.

Cross-linking reagents are used to form molecular bridges that tie together functional groups of two different molecules, e.g., a stablizing and coagulating agent. However, it is contemplated that dimers or multimers of the same analog can be made or that heteromeric complexes comprised of different analogs can be created. To link two different compounds in a step-wise manner, hetero-bifunctional cross-linkers can be used that eliminate unwanted homopolymer formation.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Preferred uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single-chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

It is particularly contemplated that antibodies will be of particular use in the various cell separation techniques described below.

IV. Cell Separation Techniques

Methods of separating cell populations and cellular subsets are well known in the art and may be applied to the cell populations of the present invention. Cells purified in this fashion may then be used for genetic engineering/gene replacement therapy. In addition, they can be used for tissue regeneration purposes. Embryonic stem cells, as well as stem cells for neuronal, endothelial, cardiac and other cell types are believed by the inventors to express functional TLR. Stimulating those stem cells from a quiescent condition with TLR ligands, mimics or agonists should be beneficial in promoting tissue regeneration, remodeling and healing. They will likely need to be used in particular combinations with previously known growth and differentiation factors. The following description sets forth exemplary methods of separation for hematopoietic stem cells based upon the surface expression of various markers, including TLRs and other cell surface markers.

A. Fluorescence Activated Cell Sorting (FACS)

FACS facilitates the quantitation and/or separation of subpopulations of cells based upon surface markers. Cells to be sorted are first tagged with a fluorescently labeled antibody or other marker specific ligand. Generally, labeled antibodies and ligands are specific for the expression of a phenotype specific cell surface molecule. The labeled cells are then passed through a laser beam and the fluorescence intensity of each cell determined. The sorter distributes the positive and negative cells into label-plus and label-minus wells at a flow rate of approximately 3000 cells per second.

The use of multiple fluorescent tags exciting at different wavelengths allows for sorting based upon multiple or alternate criteria. Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red. Thus, for example, a single PBMC sample may be analyzed with alternatively labeled anti-Ig antibody, anti-CD3 antibody, anti-CD8 antibody and anti-CD4 antibody to screen for the presence of B cells and T cells within the sample, as well as distinguishing specific T cell subsets.

FACS analysis and cell sorting is carried out on a flow cytometer. A flow cytometer generally consists of a light source, normally a laser, collection optics, electronics and a computer to translate signals to data. Scattered and emitted fluorescent light is collected by two lenses (one positioned in front of the light source and one set at right angles) and by a series of optics, beam splitters and filters, which allow for specific bands of fluorescence to be measured.

Flow cytometer apparatus permit quantitative multiparameter analysis of cellular properties at rates of several thousand cells per second. These instruments provide the ability to differentiate among cell types. Data are often displayed in one-dimensional (histogram) or two-dimensional (contour plot, scatter plot) frequency distributions of measured variables. The partitioning of multiparameter data files involves consecutive use of the interactive one- or two-dimensional graphics programs.

Quantitative analysis of multiparameter flow cytometric data for rapid cell detection consists of two stages: cell class characterization and sample processing. In general, the process of cell class characterization partitions the cell feature into cells of interest and not of interest. Then, in sample processing, each cell is classified in one of the two categories according to the region in which it falls. Analysis of the class of cells is very important, as high detection performance may be expected only if an appropriate characteristic of the cells is obtained.

Not only is cell analysis performed by flow cytometry, but so too is sorting of cells. In U.S. Pat. No. 3,826,364, an apparatus is disclosed which physically separates particles, such as functionally different cell types. In this machine, a laser provides illumination which is focused on the stream of particles by a suitable lens or lens system so that there is highly localized scatter from the particles therein. In addition, high intensity source illumination is directed onto the stream of particles for the excitation of fluorescent particles in the stream. Certain particles in the stream may be selectively charged and then separated by deflecting them into designated receptacles. A classic form of this separation is via fluorescent tagged antibodies, which are used to mark one or more cell types for separation.

Additional and alternate methods for performing flow cytometry and fluorescent antibody cell sorting are described in U.S. Pat. Nos. 4,284,412; 4,989,977; 4,498,766; 5,478,722; 4,857,451; 4,774,189; 4,767,206; 4,714,682; 5,160,974; and 4,661,913, herein expressly incorporated by reference.

B. Micro-bead Separation

Cells in suspension may be separated to very high purity according to their surface antigens using micro-bead technologies. The basic concept in micro-bead separations is to selectively bind the biomaterial of interest (e.g., a specific cell, protein, or DNA sequence) to a particle and then separate it from its surrounding matrix. Micro-bead separation involves contacting a cell suspension with a slurry of microbeads labeled with a cell surface specific antibody or ligand. Cells labeled with the micro-beads are then separated using an affinity capture method specific for some property of the beads. This format facilitates both positive and negative selection.

Magnetic beads are uniform, superparamagnetic beads generally coated with an affinity tag such as recombinant streptavidin that will bind biotinylated immunoglobulins, or other biotinylated molecules such as, for example, peptides/proteins or lectins. Magnetic beads are generally uniform micro- or nanoparticles of $Fe_3O_4$. These particles are superparamagnetic, meaning that they are attracted to a magnetic field but retain no residual magnetism after the field is removed. Suspended superparamagnetic particles tagged to a cell of interest can be removed from a matrix using a magnetic field, but they do not agglomerate (i.e., they stay suspended) after removal of the field.

A common format for separations involving superparamagnetic nanoparticles is to disperse the beads within the pores of larger microparticles. These microparticles are coated with a monoclonal antibody for a cell-surface antigen. The antibody-tagged, superparamagnetic microparticles are then introduced into a cellular suspension. The particles bind to cells expressing the surface antigen of interest and maybe separated out with the application of a magnetic field. This may be facilitated by running the suspension over a high gradient magnetic separation column placed in a strong magnetic field. The magnetically labeled cells are retained in the column while non-labeled cells pass through. When the column is removed from the magnetic field, the magnetically retained cells are eluted. Both, labeled and non-labeled fractions can be completely recovered.

C. Affinity Chromatography

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed elsewhere in this document.

V. Cells and Cell Culture

The hematopoietic progenitor cell of the present invention mice may be a multipotent progenitor (MPP) cell, a common myeloid (CMP), a granulocyte/macrophage (GMP) cell, a common lymphoid progenitor (CLP) cell, or a hematopoietic stem cell (HSC). The MPP cell based may be defined as $Lin^-IL-7R\alpha^-c-Kit^{hi}$ $Sca-1^+Flk-2^+$. The CMP cell may be defined as $Lin^-IL-7R\alpha^-c-Kit^{hi}$ $Sca-1^-$. The CMP cell may also be defined as $CD34^+Fc\gamma R^{lo}$. The GMP cell may also be defined as $Lin^-IL-7R\alpha^-c-Kit^{hi}$ $Sca-1^-CD34^+Fc\gamma R^{hi}$. The CLP cell may be defined as $Lin^-IL-7R\alpha^+c-Kit^{lo}Sca-1^{lo}$. The HSC cell may also be defined as $Lin^-IL-7R\alpha^-c-Kit^{hi}$ $Sca-1^+$ $FLK-2^-$. Long-term HSC in adult mice has been described as $Lin^-$ $Sca-1^+$ $c-Kit^{Hi}$ $Thy\ 1.1^{Lo}$ $CD150^+$ $CD34^-$ $Flk-2^-$. Human counterparts of all of these cell types have been described. For example, human HSC are enriched among the rare fraction of $Lin^-$ $CD34^+$ $CD38^-$ cells in bone marrow or umbilical cord blood.

Stem cells are generally defined as having both the capacity to self-renew (make more stem cells by cell division) as well as being able to differentiate into mature, specialized cells. A progenitor cell is an early descendant of a stem cell that can only differentiate, but it cannot renew itself anymore. In contrast, a stem cell can renew itself (make more stem cells by cell division) or it can differentiate (divide and with each cell division evolve more and more into different types of cells). A progenitor cell is often more limited in the kinds of cells it can become than a stem cell. In scientific terms, it is said that progenitor cells are more differentiated than stem cells.

Cell culture facilitates the maintenance and propagation of cells in vitro under controlled conditions. Cells may be cultured in a variety of types of vessels constructed of, for example, glass or plastic. The surfaces of culture vessels may be pre-treated or coated with, for example, collagen, polylysine, or components of the extracellular matrix, to facilitate the cellular adherence. Some sophisticated techniques utilize entire layers of adherent cells, feeder cells, which are used to support the growth of cells with more demanding growth requirements.

Cells are normally cultured under conditions designed to closely mimic those observed in vivo. In order to mimic the normal physiological environment cells are generally incubated in a $CO_2$ atmosphere with semi-synthetic growth media. Culture media is buffered and contains, among other things, amino acids, nucleotides, salts, vitamins, and also a supplement of serum such as fetal calf serum (FCS) horse serum or even human serum. Culture media may be further supplemented with growth factors and inhibitors such as hormones, transferrin, insulin, selenium, and attachment factors.

As a rule, cells grown in vitro do not organize themselves into tissues. Instead, cultured cells grow as monolayers (or in some instances as multilayers) on the surface of tissue culture dishes. The cells usually multiply until they come into contact with each other to form a monolayer and stop growing when they come into contact with each other due to contact inhibition.

Anchorage-dependent cells show the phenomenon of adherence, i.e., they grow and multiply only if attached to the inert surface of a culture dish or another suitable support. Such cells cannot normally be grown without a solid support. Many cells do not require this solid surface and show a phenomenon known as Anchorage-independent growth. Accordingly, one variant of growing these cells in culture is the use of Spinner cultures or suspension cultures in which single cells float freely in the medium and are maintained in suspension by constant stirring or agitation. This technique is particularly useful for growing large amounts of cells in batch cultures.

Anchorage-independent cells are usually capable of forming colonies in semisolid media. Some techniques have been developed that can be used also to grow anchorage-dependent cells in spinner cultures. They make use of microscopically small positively-charged dextran beads to which these cells can attach.

The starting material for the establishment of a cell culture typically is tissue from a suitable donor obtained under sterile conditions. The tissues may be minced and treated with proteolytic enzymes such as trypsin, collagenase of dispase to obtain a single cell suspension that can be used to inoculate a culture dish. In some cases dispersion of tissue is also effectively achieved by treatment with buffers containing EDTA. A particular form of initiating a cell culture is the use of tiny pieces of tissues from which cells may grow out in vitro.

Primary cell cultures maintained for several passages may undergo ascrisis. Ascrisis is usually associated with alterations of the properties of the cells and may proceed quickly or extend over many passages. Loss of contact inhibition is frequently an indication of cells having lost their normal characteristics. These cells then grow as multilayers in tissue culture dishes. The most pronounced feature of abnormal cells is the alteration in chromosome numbers, with many cells surviving this process being aneuploid. The switch to abnormal chromosome numbers is usually referred to as cell transformation and this process may give rise to cells that can then be cultivated for indefinite periods of time by serial passaging. Transformed cells give rise to continuous cell lines.

In certain aspects of the instant invention, cells are cultured prior to contact with differentiating agents such as TLR ligands. They may also be cultured after contact, i.e., after they have been induced to differentiate toward a given or specific phenotype. Cells will be cultured under specified conditions to achieve particular types of differentiation, and provided various factors necessary to facilitate the desired differentiation.

VI. Stimulatory/Inhibitory Factors

A. Cell Growth and Differentiation Factors

Cell growth and differentiation factors are molecules that stimulate cells to proliferate and/or promote differentiation of cell types into functionally mature forms. In some embodiments of the invention, cell growth and differentiation factors may be administered in combination with TLR ligands in order to direct the administered cells to proliferate and differentiate in a specific manner. One of ordinary skill would recognize that the various factors may be administered prior to, concurrently with, or subsequent to the administration of TLR ligands. In addition, administration of the growth and/or differentiation factors may be repeated as needed.

It is envisioned that a growth and/or differentiation factor may constitute a hormone, cytokine, hematapoietin, colony stimulating factor, interleukin, interferon, growth factor, other endocrine factor or combination thereof that act as intercellular mediators. Examples of such intercellular mediators are lymphokines, monokines, growth factors and traditional polypeptide hormones. Included among the growth factors are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factors-α and -β.; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β ; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte/macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; IL-13, IL-14, IL-15, IL-16, IL-17, IL-18. Also contemplated are CD14 or signal transducers of the MyD88 pathway. As used herein, the term growth and/or differentiation factors include proteins from natural sources or from recombinant cell culture and biologically active equivalents of the native sequence, including synthetic molecules and mimetics.

B. Additional Cell Surface Ligands

The CD14 antigen is a high affinity receptor for the complex of lipopolysaccharids (LPS) and LPS-Binding protein (LBP). The CD14 antigen is part of the functional heteromeric LPS receptor complex comprised of CD14, TLR4 and MD-2. CD14 is strongly expressed on most human monocytes and macrophages in peripheral blood, other body fluids and various tissues, such as lymph nodes and spleen. CD14 is weakly expressed on subpopulations of human neutrophils and myeloid dendritic cells.

The MD-2 protein appears to associate with Toll-like receptor 4 on the cell surface and confers responsiveness to lipopolysaccyaride (LPS), thus providing a link between the receptor and LPS signaling. Basic amino acid clusters in MD-2 are involved in cellular lipopolysaccharide recognition.

C. Antagonists

Soluble receptors. In one embodiment, the present invention utilize soluble forms of the TLRs of the present invention, in particular, TLR2 and TLR4. In order to render a TLR soluble, the membrane spanning regions are removed. In recombinant expression, this involves the removal of the coding regions for the membrane spanning regions. At the protein level, an appropriate protease could be used to digest the TLR to release the receptor extracellular domain. The receptor, produced recombinantly or by digestion, can be purified using antibodies that bind thereto.

Antibodies. Another agent suitable for use in blocking TLR activation is antibody that binds to the receptor without activation as would a TLR ligand. As used herein, the term "antibody" is intended to refer broadly to any appropriate immunologic binding agent such as IgG, IgM, IgA, IgD and IgE. Generally, IgG and/or IgM are preferred because they are the most common antibodies in the physiological situation and because they are most easily made in a laboratory setting.

The term "antibody" also refers to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art.

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

Single-chain antibodies are described in U.S. Pat. Nos. 4,946,778 and 5,888,773, each of which are hereby incorporated by reference. "Humanized" antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's disease are likewise known and such custom-tailored antibodies are also contemplated.

Antisense. Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

RNAi. RNA interference (also referred to as "RNA-mediated interference" or RNAi) is a mechanism by which gene expression can be reduced or eliminated. Double-stranded RNA (dsRNA) has been observed to mediate the reduction, which is a multi-step process. dsRNA activates post-transcriptional gene expression surveillance mechanisms that appear to function to defend cells from virus infection and transposon activity (Fire et al., 1998; Grishok et al., 2000; Ketting et al., 1999; Lin and Avery et al., 1999; Montgomery et al., 1998; Sharp and Zamore, 2000; Tabara et al., 1999). Activation of these mechanisms targets mature, dsRNA-complementary mRNA for destruction. RNAi offers major experimental advantages for study of gene function. These advantages include a very high specificity, ease of movement across cell membranes, and prolonged down-regulation of the targeted gene (Fire et al., 1998; Grishok et al., 2000; Ketting et al., 1999; Lin and Avery et al., 1999; Montgomery et al., 1998; Sharp et al., 1999; Sharp and Zamore, 2000; Tabara et al., 1999). Moreover, dsRNA has been shown to silence genes in a wide range of systems, including plants, protozoans, fungi, *C. elegans, Trypanasoma, Drosophila*, and mammals (Grishok et al., 2000; Sharp et al., 1999; Sharp and Zamore, 2000; Elbashir et al., 2001). It is generally accepted that RNAi acts post-transcriptionally, targeting RNA transcripts for degradation. It appears that both nuclear and cytoplasmic RNA can be targeted (Bosher and Labouesse, 2000).

siRNAs must be designed so that they are specific and effective in suppressing the expression of the genes of interest. Methods of selecting the target sequences, i.e., those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective. This length reflects the lengths of digestion products resulting from the processing of much longer RNAs as described above (Montgomery et al., 1998).

The making of siRNAs has been mainly through direct chemical synthesis; through processing of longer, double-stranded RNAs through exposure to *Drosophila* embryo lysates; or through an in vitro system derived from S2 cells. Use of cell lysates or in vitro processing may further involve the subsequent isolation of the short, 21-23 nucleotide siRNAs from the lysate, etc., making the process somewhat cumbersome and expensive. Chemical synthesis proceeds by making two single stranded RNA-oligomers followed by the annealing of the two single stranded oligomers into a double stranded RNA. Methods of chemical synthesis are diverse. Non-limiting examples are provided in U.S. Pat. Nos. 5,889,136, 4,415,723, and 4,458,066, expressly incorporated herein by reference, and in Wincott et al. (1995).

Several further modifications to siRNA sequences have been suggested in order to alter their stability or improve their effectiveness. It is suggested that synthetic complementary 21-mer RNAs having di-nucleotide overhangs (i.e., 19 complementary nucleotides+3' non-complementary dimers) may provide the greatest level of suppression. These protocols primarily use a sequence of two (2'-deoxy) thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang.

Chemically synthesized siRNAs are found to work optimally when they are in cell culture at concentrations of 25-100 nM, but concentrations of about 100 nM have achieved effective suppression of expression in mammalian cells. siRNAs have been most effective in mammalian cell culture at about 100 nM. In several instances, however, lower concentrations of chemically synthesized siRNA have been used (Caplen, et al., 2000; Elbashir et al., 2001).

WO 99/32619 and WO 01/68836 suggest that RNA for use in siRNA may be chemically or enzymatically synthesized. Both of these texts are incorporated herein in their entirety by reference. The enzymatic synthesis contemplated in these references is by a cellular RNA polymerase or a bacteriophage RNA polymerase (e.g., T3, T7, SP6) via the use and production of an expression construct as is known in the art. For example, see U.S. Pat. No. 5,795,715. The contemplated constructs provide templates that produce RNAs that contain nucleotide sequences identical to a portion of the target gene. The length of identical sequences provided by these references is at least 25 bases, and may be as many as 400 or more bases in length. An important aspect of this reference is that the authors contemplate digesting longer dsRNAs to 21-25 mer lengths with the endogenous nuclease complex that converts long dsRNAs to siRNAs in vivo. They do not describe or present data for synthesizing and using in vitro transcribed 21-25 mer dsRNAs. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. Preferably, single-stranded RNA is enzymatically synthesized from the PCR products of a DNA template, preferably a cloned cDNA template and the RNA product is a complete transcript of the cDNA, which may comprise hundreds of nucleotides. WO 01/36646, incorporated herein by reference, places no limitation upon the manner in which the siRNA is synthesized, providing that the RNA may be synthesized in vitro or in vivo, using manual and/or automated procedures. This reference also provides that in vitro synthesis may be chemical or enzymatic, for example using cloned RNA polymerase (e.g., T3, T7, SP6) for transcription of the endogenous DNA (or cDNA) template, or a mixture of both. Again, no distinction in the desirable properties for use in RNA interference is made between chemically or enzymatically synthesized siRNA.

U.S. Pat. No. 5,795,715 reports the simultaneous transcription of two complementary DNA sequence strands in a single reaction mixture, wherein the two transcripts are immediately hybridized. The templates used are preferably of between 40 and 100 base pairs, and which is equipped at each end with a promoter sequence. The templates are preferably attached to a solid surface. After transcription with RNA polymerase, the resulting dsRNA fragments may be used for detecting and/or assaying nucleic acid target sequences.

Ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Morpholino oligos. Morpholino oligos are so named because they are assembled from four different morpholino subunits, each of which contains one of the four bases—adenine, cytosine, guanine, and thymine—linked to a 6-membered morpholine ring. These bases are joined by non-ionic phosphorodiamidate intersubunit linkages to give a morpholino oligo. Morpholino oligonucleotides (MOs) are a powerful approach to loss of function analysis in Xenopus embryos. Unlike dominant negative constructs, they have the advantage of increased specificity for the particular targeted gene.

VII. Methods

A method for stimulating hematopoietic stem cells (HSC) with Toll-like receptor (TLR) ligands, antibodies to TLR or mimics of TLR ligands is provided herein. The discovery involves, in part, the observation that highly purified HSC express functional TLR. Ligation of TLR2 or TLR4 with $Pam_3CSK_4$ or lipopolysaccharide, respectively activates HSC from quiescence. This would be desirable in circumstances where HSC need to be expanded for transplantation and other applications. Additional TLRs on HSC are presumably functional, and stimulating via single TLR or combinations of TLRs may be advantageous for directing particular stem cell responses. Antibodies to TLRs or small molecules resembling TLR ligands may be used in place of bacterial/viral products to elicit desirable responses in stem cells. Agents that act downstream of these receptors on intracellular signaling pathway mediators such as MyD88, TRAM or TRIF could also be used in this fashion.

Another embodiment is directed to methods for stimulating myeloid progenitor cells with TLR ligands, antibodies to TLRs or mimics of TLR ligands. The present inventors have discovered that highly purified progenitors can be stimulated in the absence of normal growth and differentiation factors by ligating TLR. Therefore, agonists of TLRs can be used alone, or as complementary agents with colony stimulating factors and cytokines, to stimulate or regulate blood cell formation.

Yet another embodiment provides for methods of directing hematopoietic stem/progenitor cells to replenish the innate immune system by stimulating them with TLR ligands. Lymphoid progenitor cell are surprisingly able to be directed to become myeloid dendritic cells rather than lymphocytes when exposed to TLR ligands. These dendritic cells are known to provide some aspects of innate immunity, and participate in specific, adaptive immune responses. TLR agonists can thus be used to boost production of myeloid dendritic cells, particularly in an immunodeficient or immunocompromised patient.

Another method disclosed herein is the use of TLR antagonists to protect hematopoietic stem/progenitor cells during immunosuppression, myeloablation, bone marrow transplantation or chronic infection. The inventors' findings reveal that stem cells can be depleted, exhausted, aged or otherwise harmed by unwanted stimulation via TLR. A particularly useful form of this method is the maintenance of stem cell quiescence during chemotherapy. Any agent that blocks activation via TLR or downstream intracellular mediators would be protective under these circumstances. Another aspect of this embodiment is preventing overproduction of cells in the innate immune system in autoimmune diseases. Yet another aspect of TLR inhibition could be the protection of fetuses from intrauterine infections, as activation of fetal hematopoietic cells via TLR ligands may cause abortion or damage to the fetus.

The present invention also contemplates the use of TLR agonists in methods to protect hematopoietic stem/progenitor cells from differentiation into non-hematopoietic cells. The inventors' findings, based on the discovery that early hematopoietic progenitor cells exhibit function TLRs, reveal that stem cells can be depleted, exhausted, aged or otherwise harmed by unwanted stimulation via TLR.

Thus, the present invention contemplates various situations where TLR antagonists will be used to protect stem cells and insure their development into hematopoietic cells, such as in the context of bone marrow regrafting following ablative chemo- or radiotherapy. Such methods will involve the use of the antagonists discussed elsewhere in this document in both in vivo and ex vivo contexts. Methods for ablative therapies are well known to those of skill in the art and can be combined, advantageously, with the stem cell protective methods of the present invention.

VIII. Pharmaceutical Compositions

It is envisioned that, for administration to a host, TLR ligands, other cell surface ligands, cytokines or growth factors, soluble TLRs, antibodies, other inhibitory factors, and stimulated/differentiated cells will be suspended in a formulation suitable for administration to a host. Aqueous compositions of the present invention comprise an effective amount of ligand, factor or cells dispersed in a pharmaceutically acceptable formulation and/or aqueous medium. The phrases "pharmaceutically and/or pharmacologically acceptable" refer to compositions that do not produce an adverse, allergic and/or other untoward reaction when administered to an animal, and specifically to humans, as appropriate.

As used herein, "pharmaceutically acceptable carrier" includes any solvents, dispersion media, coatings, antibacterial and/or antifungal agents, isotonic and/or absorption delaying agents and the like. The use of such media or agents for pharmaceutical active substances is well known in the art. Except insofar as any conventional media or agent is incompatible with the active ingredient, its use in the therapeutic compositions is contemplated. Supplementary active ingredients can also be incorporated into the compositions. For administration to humans, preparations should meet sterility, pyrogenicity, general safety and/or purity standards as required by FDA Office of Biologics standards.

Soluble receptors, antibodies, inhibitory factors or cells, ligands, or cells for administration will generally be formulated for parenteral administration, e.g., formulated for injection via the intravenous, intramuscular, sub-cutaneous, intralesional, or even intraperitoneal routes. The preparation of an aqueous composition that contains cells as a viable component or ingredient will be known to those of skill in the art in light of the present disclosure. In all cases the form should be sterile and must be fluid to the extent that easy syringability exists and that viability of the cells is maintained. It is generally contemplated that the majority of culture media will be removed from cells prior to administration.

Generally, dispersions are prepared by incorporating the various soluble receptors, antibodies, inhibitory factors, or viable cells into a sterile vehicle which contains the basic dispersion medium and the required other ingredients for maintaining cell viability as well as potentially additional components to effect proliferation or differentiation in vivo. Upon formulation, solutions will be administered in a manner compatible with the dosage formulation or in such amount as is therapeutically effective. Some variation in dosage will necessarily occur depending on the condition of the subject being treated. The person responsible for administration will, in any event, determine the appropriate dose for the individual subject.

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

Mice. C57BL/6 and MyD88$^{-/-}$ mice were used at 8-10 weeks of age. C57BL/6 mice were purchased from the Jackson Laboratory (Bar Harbor, Me.). MyD88$^{-/-}$ mice were maintained in our laboratory animal resource facility (LARC) at the Oklahoma Medical Research Foundation.

Reagents. Recombinant mouse IL7, stem cell factor (SCF), Flt-3 ligand (FL), M-CSF, GM-CSF, recombinant mouse CD14/Fc chimera protein, and recombinant human CD14 were purchased from R&D Systems (Minneapolis, Minn.). LPS from *Escherichia coli* 055:B5 was purchased from Sigma-Aldrich (St. Louis, Mo.). A synthetic lipopeptide Pam$_3$CSK$_4$ was purchased from InvivoGen (San Diego, Calif.).

Antibodies and flow cytometry. The following Abs for flow cytometry were purchased from eBioscience (San Diego, Calif.): biotinylated anti-TLR4/MD-2 (clone MTS510), biotinylated anti-RP105 (clone RP/14), biotinylated anti-MD-1 (clone MD113), biotinylated anti-CD14 (clone Sa2-8), PE-conjugated anti-CD62L (clone MEL-14), allophycocyanin (APC)-conjugated anti-F4/80 (clone BM8), anti-c-Kit (clone ACK2), phycoerythrin (PE)-Cy5-conjugated anti-Sca-1 (clone D7), biotinylated anti-Flk-2 (clone A2F10), purified anti-mouse CD115 (CSF-1R, clone AFS98), purified anti-mouse GM-CSF (clone MP 1-22E9), and purified anti-mouse TNFα (clone MP6-XT22).

The following Abs for flow cytometry were purchased from BD Pharmingen (San Diego, Calif.): FITC-conjugated anti-CD2 (clone RM2-5), anti-CD3ε (clone 145-2C11), anti-CD8α (clone 53-6.7), anti-CD45R (B220; clone RA3-6B2), anti-Ly6G (clone RB6-8C5), anti-CD11b/Mac-1 (clone M1/70), anti-TER119, anti-CD34 (clone RAM34), anti-CD11c (clone HL3), PE-conjugated IL-7Rα (clone SB/119), anti-CD19 (clone 1D3), anti-Ly6G (clone RB6-8C5), anti-CD11c (clone HL3), anti-FcγR2/3 (clone 2.4G2), anti-AA4.1, anti-CD86 (clone GL1), APC-conjugated anti-CD45R (clone RA3-6B2), anti-CD11b/Mac-1 (clone M1/70), biotin-conjugated anti-VCAM-1 (clone 429, MVCAM.A) PE-conjugated streptavidin and PE Texas-Red-conjugated streptavidin. For analyzing cultured cells by flow cytometry, 7-AAD (BD Pharmingen) was always used to exclude dead cells.

Flow cytometry analyses was conducted on a FACSCan™, FACSCalibur™ or FACSAria™ (Becton Dickinson & Co., Mountain View, Calif.), and the data were analyzed with FlowJo software (Treestar, San Carlos, Calif.).

Establishment of the anti-mouse TLR4 monoclonal antibody (clone UT49). A full description of the preparation and validation of this reagent will be published elsewhere. Briefly, TLR4-deficient mice were intraperitoneally injected four times at a week intervals with 1×10$^7$ Ba/F3 cells expressing mouse TLR4 and mouse MD-2. Three days after the last injection, mice were euthanized and spleens were removed. Spleen cells were dispersed and fused with SP2/O cells using a standard fusion protocol with polyethylene glycol 1500 (Roche, Basel, Switzerland). Hybridoma cells were selected in hypoxanthine/aminopterine/thymidine medium and screened by flow cytometry with Ba/F3 cells expressing mouse TLR4/MD-2 complex and parent Ba/F3 cells. Biotin-conjugated this antibody was used for flow cytometry.

Isolation of stem and progenitor cells. Bone marrow cells were harvested and enriched for lineage-negative cells by incubation with antibody to CD b/Mac-1 (clone M1/70), anti-Ly6G (clone RB6-8C5), anti-CD45R (B220; clone RA3-6B2), anti-CD19 (clone 1D3) and anti-TER119, followed by negative selection using the MACS cell separation system (Miltenyi Biotec, Auburn, Calif.). For sorting of Flk-2$^-$ or Flk-2$^+$ LKS$^+$ (Lin$^-$ IL-7Rα$^-$ c-Kit$^{hi}$ Sca-1$^+$), LKS$^-$(Lin$^-$ IL-7Rα$^-$ c-Kit$^{hi}$ Sca-1$^-$) and CLP (Lin$^-$ IL-7Rα$^+$ c-Kit$^{lo}$ Sca-1$^{lo}$), these partially lineage-depleted cells were further stained with FITC-conjugated lineage markers; anti-CD2, anti-CD3ε, anti-CD8α, anti-CD45R, anti-Ly6G, anti-CD11b/Mac-1, anti-TER119, PE-conjugated IL-7Rα, APC-conjugated anti-c-Kit, PE-Cy5-conjugated anti-Sca-1, and biotinylated anti-Flk-2 combined with PE Texas-Red conjugated streptavidin. For sorting of CMP (Lin$^-$ IL-7Rα$^-$ c-Kit$^{hi}$ Sca-1$^-$ CD34$^+$ FcγR2/3$^{lo}$), GMP (Lin$^-$ IL-7Rα$^-$ c-Kit$^{hi}$ Sca- 1⁻ CD34⁺ FcγR2/3$^{hi}$) and MEP (Lin⁻ IL-7Rα⁻ c-Kit$^{hi}$ Sca-1⁻ CD34⁻ FcγR2/3$^{lo}$), the sorted LKS⁻ cells were further stained with FITC-conjugated anti-CD34 and PE-conjugated anti-FcγR2/3. Cells were sorted on a FACSAria™ (Becton Dickinson & Co.)

Serum-free, stromal cell-free cell cultures. Round-bottomed 96-well plates or flat-bottomed 24-well plates (Corning Inc.) were used for these cultures. Sorted cells were cultured with X-VIVO15 medium (Biowhittaker, Walkersville, Md.) or StemPro-34 SFM medium (Invitrogen, Carlsbad, Calif.). X-VIVO15 medium, that seemed to be optimal for lymphoid cultures, contained 1% detoxified bovine serum albumin (Stem Cell Technologies, Vancouver, Canada), $5 \times 10^{-5}$ M 2-mercaptoethanol (2-ME), 2 mM L-glutamine, 100 U/ml penicillin and 100 mg/ml streptomycin. StemPro-34 SFM medium containing 2 mM L-glutamine, 100 U/ml penicillin and 100 mg/ml streptomycin was usually used for myeloid cultures. The concentrations of cytokines were IL-7, 1 ng/ml; FL, 100 ng/ml; SCF, 20 ng/ml, M-CSF, 20 ng/ml; GM-CSF, 20 ng/ml. The cells were incubated at 37° C. in a humidified atmosphere of 5% $CO_2$ in air.

Single cell culture on OP9 stromal cells. Sorted CLP were cultured with X-VIVO15 in the presence of SCF (20 ng/ml), FL (100 ng/ml) and IL-7 (1 ng/ml) with or without LPS (10 μg/ml), or Pam₃CSK₄ (1 μg/ml). After 24 h, cultured cells were harvested and washed with medium three times. A single cell sorting for the cultured cells was then conducted on a FACSAria™ and a single cell was plated on OP9 stromal cells in 96-well plate and cultured for 10 days in the presence of SCF (20 ng/ml), FL (100 ng/ml) and IL-7 (1 ng/ml). The conditioning medium for OP9 was MEMα medium (Invitrogen) containing 20% FCS, $5 \times 10^{-5}$ M 2-ME, 2 mM L-glutamine, 100 U/ml penicillin and 100 mg/ml streptomycin. Positive wells (more than 30 cells) were determined by microscopic observation. Cells were harvested and then stained with mAbs to CD19, CD11c, and Mac-1 and analyzed by flow cytometry. Cells were also stained with mAb to VCAM-1 to exclude stromal cells. The OP9 stromal cell line was kindly provided by Dr. Shin-Ichi Hayashi (Tottori University, Japan).

In vitro BrdU incorporation. Sorted Flk-2⁻ LKS⁺ cells (10,000 cells/well) were cultured with or without LPS (10 μg/ml) or Pam₃CSK₄ (1 μg/ml) in the presence of SCF (20 ng/ml) for 50 h, pulsing with 10 μM 5-bromo-2'-deoxyuridine (BrdU) for the final 18 h. The cells were then stained with anti-BrdU. BrdU flow kit was purchased from BD Pharmingen. Analyses by flow cytometry were conducted on a FACScan™.

Interaction of LPS with the TLR4/MD-2 complex. Whole bone marrow cells from C57BL/6 mice were cultured in RPMI1640 medium (Mediatech, Inc. Herndon, Va.) containing 10% FCS, $5 \times 10^{-5}$ M 2-ME, 2 mM L-glutamine, 100 U/ml penicillin, and 100 mg/ml streptomycin and stimulated with or without 1 μg/ml LPS for 1 h. Then cells were harvested and stained with mAbs to TLR4/MD-2, Mac-1, lineage markers (CD2, CD3e, CD8a, CD45R/B220, CD11b/Mac-1, Ly6G, TER119), and c-Kit. Alternatively, C57BL/6 mice were intravenously or intraperitoneally injected with PBS or 100 μg LPS. After 1 h, whole bone marrow cells were harvested from femurs and tibiae, and stained with mAbs to TLR4/MD-2, Mac-1, lineage markers, and c-Kit. The MTS 10 reagent is unique in detecting a conformation dependent epitope on TLR4/MD-2 (Gilliet et al., 2002).

Cell morphology. Cytospins of cultured progenitor cells were stained with Giemsa-May-Grünwald (Sigma Diagnostics, St. Louis, Mo.), mounted in Immersol (Zeiss, Thornwood, N.Y.), and analyzed on a Zeiss Axioplan 2i microscope with a 100×/1.4 NA Plan Achromat objective. Photomicrographs were made using an AxioCam MRc color camera (Zeiss), and AxioVision 3.1 software (Zeiss).

Reverse transcriptase (RT)-PCR analysis of gene expression. The mRNAs were isolated from sorted cells using MicroPoly(A) Pure (Ambion, Austin, Tex.). The cDNAs were then prepared from DNase I-treated mRNA using oligo-dT and Moloney murine leukemia virus reverse transcriptase (Invitrogen). PCR reactions were conducted in buffer containing 200 μM dATP, dGTP, dTTP, 100 μM dCTP and 0.5 μCi [α $^{32}$P] dCTP. Aliquots were removed at cycle 25, 28 and 31 for β-actin and cycles 32, 35 and 38 for all others to insure that PCR remained within the exponential range of amplifications. Five microliter aliquots were denatured in a formamide-loading buffer and applied to a 6% polyacrylamide gel containing 7 M urea. Incorporation of [α $^{32}$P] dCTP into PCR product bands was quantified by PhospholImager (Molecular Dynamics, Sunnyvale, Calif.). The primer sequences for each gene are given in Table 1.

Statistical analysis. The statistical significance of differences between group means was determined with the Student's t-test. P values less than 0.05 were considered significant.

Example 2

Results

Toll-like receptors and associated molecules are expressed on stem cells and early hematopoietic progenitors. The main aims of this study were to determine if TLRs are expressed on hematopoietic cells and whether they have a developmental role in bone marrow. Therefore, the inventors traced the expression of TLRs and their co-receptors on bone marrow cells by flow cytometry and were fortunate to have a new TLR4 specific monoclonal antibody (see Example 1). An initial finding was that lineage marker negative (Lin⁻), as well as Lin⁺ cells expressed TLR2 and TLR4 as well as MD-2 and CD14 (FIG. 9A). HSC and early progenitors are enriched in a Lin⁻ c-Kit⁺ subset. These primitive cells displayed significant amounts of TLRs and co-receptor components (FIG. 9A).

Next, the inventors divided Lin⁻ c-Kit⁺ cells into five major subsets and evaluated them by flow cytometry (FIG. 1A). The HSC enriched Lin⁻ IL-7Rα⁻ c-Kit$^{hi}$ Sca-1⁺ (LKS⁺) fraction had uniformly high levels of TLR2, and the same was true for Lin⁻ IL-7Rα⁺ c-Kit$^{lo}$ Sca-1$^{lo}$, pro-lymphocytes/common lymphoid progenitors (CLP). The Lin⁻ IL-7Rα⁻ c-Kit$^{hi}$ Sca-1⁻ (LKS⁻) myeloid/erythroid progenitor fraction was heterogeneous with respect to TLR2 staining (data not shown). Then, this fraction was sub-divided on the basis of CD34 and FcγR levels (Akashi et al., 2000). Unlike the other fractions, Lin⁻ IL-7Rα⁻ c-Kit$^{hi}$ Sca-1⁻ CD34⁻ FcγR$^{lo}$ megakaryocyte/erythrocyte progenitors (MEP) had very little TLR2 (FIG. 1A). The Lin⁻ IL-7Rα⁻ c-Kit$^{hi}$ Sca-1⁻ CD34⁺ FcγR$^{hi}$ granulocyte/macrophage progenitors (GMP) subset was uniformly TLR2⁺ and Lin⁻ IL-7Rα⁻ c-Kit$^{hi}$ Sca-1⁻ CD34⁺ FcγR$^{lo}$ common myeloid progenitors (CMP) were heterogeneous with respect to this receptor (FIG. 1A). In fact, the density of FcγR corresponded well with TLR2 expression on LKS⁻ cells as a whole (FIG. 1B). A new TLR4 specific antibody or one directed to the TLR4/MD-2 complex stained the HSC enriched fraction and CD14 was also conspicuous. In contrast to HSC, CLP were very similar to mature spleen B cells that have a high density of TLR2 and trace amounts of TLR4/

MD-2 or CD14 (Nagai et al., 2005). TLR4 and CD14 were more easily seen on GMP than the two LSK⁻ companion subsets (FIG. 1A).

Some TLRs are not displayed on the cell surface so each of the above fractions was analyzed by RT-PCR (FIG. 1B). In general, there was good correlation between transcript levels and flow cytometry results. Long term repopulating HSC are known to be enriched in the Flk-2⁻ subset of the LKS⁺ fraction (Christensen and Weissman, 2001). Interestingly, this population had the highest levels of TLR2, TLR4, and MD-2 mRNA, but little CD14.

This analysis was extended by staining progenitors with antibodies to RP105 and MD-1 (FIG. 10). RP105 forms a complex with MD-1 (Miyake et al., 1998; Nagai et al., 2002) and controls Ab responses to microbial membranes via TLR2 and TLR4/MD-2 (Nagai et al., 2005). It has been reported that, unlike the situation with B cells, RP105 can be a negative regulator of TLR4 signaling on macrophages (Divanovic et al., 2005). The inventors have now found that three populations of Lin⁺ bone marrow cells could be distinguished on the basis of densities of the RP105/MD-1 complex. Less RP105/MD-1 was present on Lin⁻ or Lin⁻ c-Kit⁺ cells. Among the progenitors, RP105 was highest on CLP, detectable on GMP and near background on the other subsets. The density of MD-1 on most of these progenitors corresponded with RP105 expression.

The inventors conclude that the most primitive of hematopoietic progenitors in bone marrow, and especially a rare stem cell enriched fraction, express TLRs and associated molecules.

TLR signaling drives MyD88-dependent myeloid differentiation of primitive hematopoietic cells. The experiments next focused on potential functions for TLRs on hematopoietic progenitors. The inventors isolated LKS⁺ cells and stimulated them in serum-free, stromal cell-free cultures with either LPS, a TLR4 ligand or Pam₃CSK₄, a ligand for TLR2. It was determined in preliminary experiments that the cytokines FL and SCF promoted cell viability, but alone caused little differentiation under these conditions. The frequency of Lin⁺ cells increased as a result of TLR stimulation in as little as 24 h and progressed with time (FIG. 2A and FIG. 11A). Absolute numbers of Lin⁺ cells increased approximately eight-fold within 72 h, and this response did not occur with cells from MyD88-deficient mice (FIG. 2A). Expanding cells expressed the CD11b/Mac-1 and/or Gr-1 myeloid markers, but not CD45R/B220 (FIG. 2B). The mature monocyte/macrophage marker F4/80 was acquired by some cells in as little as 72 h and increased dramatically with time (FIG. 2C). In parallel with these changes, substantial numbers of LKS⁺ bone marrow cells acquired the FcγR2/3 in response to LPS or Pam₃CSK₄ exposure within 24 h (data not shown).

The dose of LPS required to stimulate hematopoietic cells under serum-free conditions was high, and the inventors found minimal responses at concentrations below 10 µg/ml (FIG. 2D). Serum is known to contain soluble CD14 that enhances LPS and TLR2 ligand recognition by mature cells (Yoshimura et al., 1999; Means et al., 1999). Therefore, the inventors added mouse CD14-Fc protein to this culture system and found that it remarkably augmented the sensitivity of LKS⁺ cells to LPS after 72 h (FIG. 2d and FIG. 11B). That is, the inventors recorded responses to as little as 0.1 µg/ml LPS and found co-expression of CD11b/Mac-1 and F4/80 within 72 h (FIG. 3B). A recombinant human CD14 was similar to mouse CD14-Fc in augmenting LPS responses (data not shown). Exogenous CD14 had less influence on responses to Pam₃CSK₄ (FIG. 2D).

Similar studies were performed with the LSK⁺ fraction subdivided on the basis of Flk-2 (FIG. 3A). This revealed that the long term repopulating stem cell rich Flk-2⁻ subset responded to TLR stimulation, but less dramatically than multipotent Flk-2⁺ progenitors. BrdU labeling experiments were then done to learn if the quiescent long-term repopulating HSC subset could be driven into cycle by TLR ligation (FIG. 3B). This was indeed the case, and increased proportions of stimulated cells incorporated the proliferation label.

A preliminary RT-PCR analysis was performed with the same experimental design to verify TLR ligand induced differentiation. The stem cell rich Lin⁻ c-Kit$^{hi}$ Sca-1⁺ Flk-2⁻ fraction was cultured with or without TLR ligands for 24 h. Transcripts for the M-CSF receptor (c-fms) increased on stimulation with TLR ligands, consistent with monocyte/macrophage differentiation, but the GM-CSF receptor was expressed at substantial levels and unchanged (FIG. 12). Another objective was to determine if key transcription factors associated with lineage fate decisions were altered. Depression of SCL and GATA2 transcripts and a slight increase in PU.1 were seen as expected for myeloid progenitors (Akashi et al., 2000). However, the C/EBPα transcription factor that can drive macrophage differentiation (Rosmarin et al., 2005; Xie et al., 2004) declined unexpectedly with TLR stimulation (FIG. 12).

It is clear from these findings that two TLR ligands delivered MyD88-dependent signals, promoting myeloid lineage progression of primitive hematopoietic cells. Moreover, highly enriched populations of HSC displayed functional receptors for these substances. Soluble CD14 dramatically augmented the sensitivity to LPS, but not Pam₃CSK₄.

Figure 13:
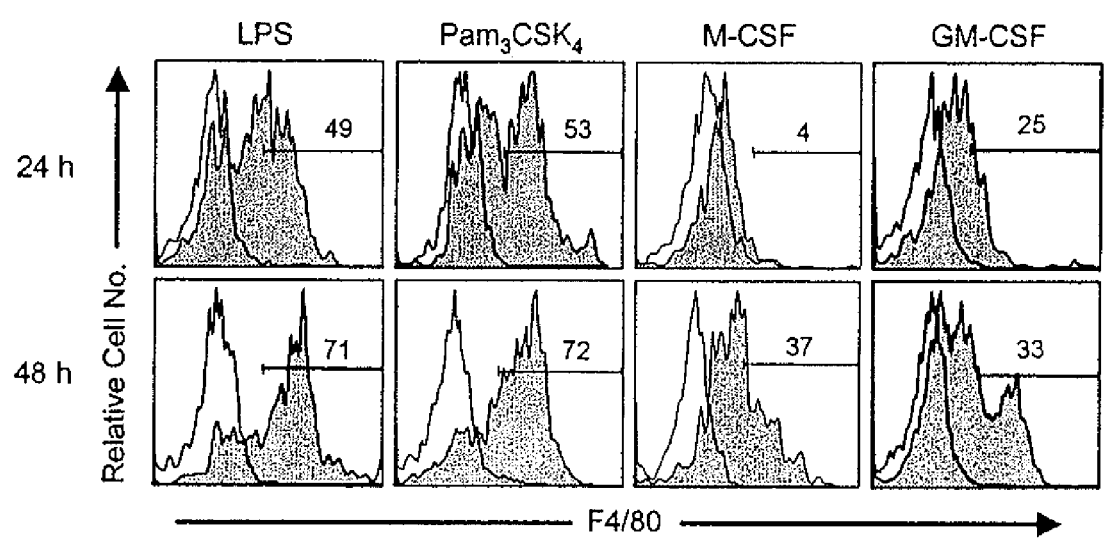
FIG. 13—TLR stimulation causes rapid production of F4/80+ cells from LKS− cells. Sorted LKS cells (10,000 cells/well) from C57BL/6 mice were cultured with LPS (10 μg/ml), Pam$_3$CSK$_4$ (1 μg/ml), M-CSF, or GM-CSF. Virtually no viable cells were recovered from wells with no stimulus and were not studied further. Stimulated wells were analyzed after 24 h or 48 h of culture by flow cytometry for expression of F4/80. Open histograms depict staining with the isotype matched Ab for F4/80. Percentages of F4/80+ cells are representative of three independent experiments.

Signaling via TLRs on granulocyte/macrophage progenitors obviates the need for growth and differentiation factors. The above findings show that highly enriched hematopoietic stem cells can be stimulated via TLRs to produce myeloid lineage cells. The inventors next asked if LKS⁻ committed myeloid/erythroid progenitors would be similarly responsive. Serum-free, stromal cell free culture conditions were used to determine whether the normal cues for differentiation might be overcome. Acquisition of F4/80 was dramatic and complete in response to TLR ligands (FIG. 4A). In fact, responses at 72 h were indistinguishable from those obtained when the same population was stimulated with M-CSF. In contrast to those three differentiation stimuli, only a subset of LKS⁻ myeloid progenitors responded to GM-CSF. While signaling via TLR is dependent on MyD88, this was not the case for these CSFs (FIGS. 4A-B). In some experiments, yields of F4/80⁺ cells obtained with LPS were nearly equal to those derived with CSF stimulation, while Pam₃CSK₄ was consistently a less potent stimulus (FIG. 4B). Shorter culture intervals were used to compare TLR and CSF receptor signaling (FIG. 13). TLR ligands caused rapid acquisition of F4/80 that was apparent 24 h or 48 h after stimulation.

It seemed possible that the hematopoietic cells were induced to produce their own growth and differentiation factors. Therefore, neutralizing monoclonal antibodies to either M-CSF receptor or GM-CSF were added to the culture system (FIG. 4C). Although the amounts used were sufficient to completely block responses to M-CSF, and greatly diminish those to GM-CSF, the antibodies had no significant effect on TLR stimulation.

Three subsets of LKS⁻ cells were then sorted and stimulated with TLR ligands (FIG. 4D) to precisely identify cellular targets for TLR stimulation. MEP died in culture, regardless of stimulus, and the inventors never recovered cells expressing the erythrocyte associated TER119 marker (data not shown). In contrast, GMP produced F4/80⁺ cells within 24 h (FIG. 4D). While CMP also responded, more time was required, and the calculated yield of F4/80+ at 72 h was much less. Addition of exogenous CD14 to this culture augmented stimulation via TLRs (data not shown), but less than that described above for stem cells.

The inventors conclude that myeloid progenitors representing a range of differentiation stages react to TLR ligands via a MyD88-dependent pathway under defined culture conditions and typical growth and differentiation factors are not required. GMP represented the most responsive of myeloid/ erythroid progenitors in bone marrow. The responses were distinct from those observed with CSFs in terms of time required and dependence on MyD88.

Monocyte/macrophage subsets are rapidly produced from committed myeloid progenitors. The inventors wondered if a normal range of myeloid cell types would be produced in response to TLR ligation. Accordingly, GMPs were placed in defined culture conditions for 72 h, and the recovered cells were subjected to thorough analysis (FIGS. 5A-C). In contrast to cultures stimulated with M-CSF or GM-CSF, where typical foamy macrophages or neutrophils predominated, macrophage-like cells in LPS containing cultures had more basophilic cytoplasms with small granules. Cells recovered from $Pam_3CSK_4$ stimulated cultures were less homogeneous in appearance (FIG. 5A). Virtually all cells produced in response to LPS or $Pam_3CSK_4$ were CD11b/Mac-1+ but heterogeneous with respect to densities, and this tended to correlate with the density of F4/80 (FIG. 5B). A conspicuous subset of Mac-1+ F4/80− cells in response to GM-CSF were not present in TLR ligand cultures. LPS was particularly efficient in driving production of Mac-1$^{hi}$ F4/80$^{hi}$ cells (FIG. 5C). Previous studies showed that Gr-1 and CD62L are present on inflammatory Mac-1+ F4/80+ monocytes but not on ones destined to reside in normal tissues (Geissman et al., 2003). This inflammatory phenotype was on TLR ligand or GM-CSF stimulated Mac-1$^{hi}$ F4/80$^{hi}$ cells but not on M-CSF stimulated cells (FIG. 5B). The co-stimulatory CD86 molecule was present on TLR generated cells, but less than that on cells made with M-CSF. Additionally, only 9% of the cells recovered from LPS stimulated cultures displayed both Mac-1 and CD11c markers associated with DCs within 72 h, and none were found in any of the other cultures (data not shown).

These results indicate that TLR stimulation allows committed myeloid progenitors to differentiate into Mac-1$^{hi}$ F4/80$^{hi}$ monocytes/macrophages with inflammatory characteristics independent of exogenous growth factors. This could represent an effective mechanism for responding to pathogens and sustaining multifunctional cells of the innate immune system.

Myeloid dendritic cell production at the expense of lymphopoiesis in response to TLR ligands. The experiments were then extended to a consideration of lymphoid biased progenitors. Under experimental conditions, CLP can give rise to T, B, NK and DCs (Kouro et al., 2002; Karsunky et al., 2003; Shigematsu et al., 2004). Almost pure populations of CD19+ B lineage cells are produced when CLP are placed in serum-free, stromal cell-free culture with cytokines (FIG. 6A). However, only Mac-1+ cells emerged when LPS was added, and a mixture of the two cell types was found in $Pam_3CSK_4$ containing cultures. This dramatic change was dependent on MyD88 as only CD19+ lymphocytes were produced in cultures initiated with CLPs from MyD88-deficient mice. Most Mac-1+ cells had myeloid DC morphology on Giemsa-May-Grünwald stained slides (FIG. 6B). Further analysis of these cultures revealed that almost all of the Mac-1+ cells produced from CLP in response to LPS were CD11c+ Gr-1− (FIG. 6C). Cells recovered from $Pam_3CSK_4$ containing cultures were Gr-1− but less homogenous.

It seemed possible that TLR ligation induced production of cytokines that could then drive the differentiation observed. GM-CSF and TNFα were of particular interest because they can promote the production of myeloid DCs from bone marrow in vitro (Gilliet et al., 2002). In addition, TNFA can suppress B-lymphopoiesis (Sedger et al., 2002). However, neutralizing antibodies to either GM-CSF or TNFα did not suppress the production of DCs from CLPs induced by TLR ligands (data not shown).

As described above (FIGS. 1A-B), CLP express little TLR4/MD-2 or CD14 that is detectable by flow cytometry as mature B cells. Since the experiments described in FIG. 6A were conducted with serum-free medium, exogenous CD14 was added to the cultures to determine if this would influence efficiency of TLR4/MD-2 signals. Indeed, exogenous CD14 dramatically augmented DC production by low doses of LPS in serum-free cultures (FIG. 6D). In contrast, exogenous CD14 had little effect on responses to any dose of $Pam_3CSK_4$ (data not shown).

Although CLP are largely B lineage restricted when held in defined conditions, these progenitors produce DCs in stromal cell co-cultures and transplantation assays (Karsunky et al., 2003; Shigematsu et al., 2004). It seemed possible that TLR ligation substitutes for that permissive signal and selects for clones that are not fully B lineage committed. Therefore, CLP were sorted to high purity and incubated for 24 h with LPS, $Pam_3CSK_4$ or medium alone. Each group of cells was then harvested, and single cells were plated on OP9 stromal cells with cytokines to assess differentiation potential (FIG. 7). Four types of clones were detected ten days later. Without TLR ligands, CLP produced not only pure CD19+ B lineage but also CD11c+ or CD11c+ CD19+ mixed colonies, or colonies that were CD11c− CD19−. Pure B cell colonies were the largest in this situation (data not shown). Most of the CD11c+ cells were also CD11b/Mac-1+ and in myeloid DC or mixed colonies were very small (data not shown). Numbers of pure B cell clones consistently declined when LPS was present, while the same treatment increased numbers of pure mDC colonies. $Pam_3CSK_4$ also enhanced production of colonies with pure mDC, but did not alter the production of CD19+ B cell clones. Thus, the results of these clonal assays concur with those obtained with serum-free, stromal-cell free bulk cultures (FIGS. 6A & 6D).

Figure 14:
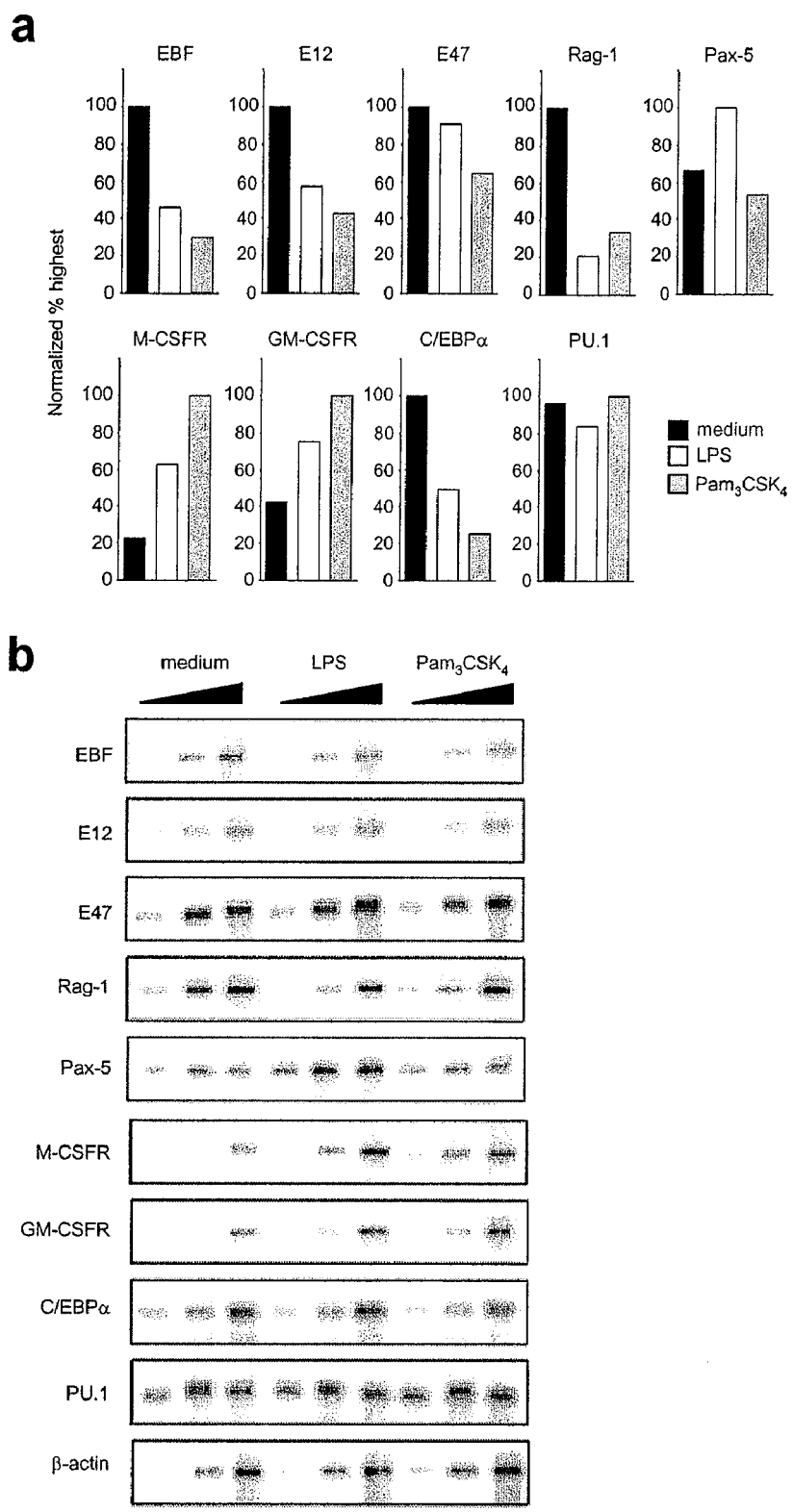
FIGS. 14A-B—Alteration of some lineage-associated gene patterns in TLR ligated CLPs. Sorted CLP from C57BL/6 mice were stimulated with medium alone, LPS (10 μg/ml) or Pam$_3$CSK$_4$ (1 μg/ml) in the presence of IL-7, FL, and SCF. After 24 h in culture, cells were harvested and mRNAs were isolated from cultured cells. Semi-quantitative RT-PCR was carried out to amplify transcripts for the indicated genes in each population.

RT-PCR was then used to evaluate CLP 24 h after stimulation with TLR ligands (FIG. 14). As might be expected with maturing DCs, transcripts corresponding to GM-CSF receptors increased with stimulation. Reductions were recorded in the EBF, E12 and RAG-1 transcription factors required for lymphopoiesis, in parallel with increases in M-CSF receptor, but changes in three others, PU.1, E47 and Pax-5, were not remarkable. As noted above for stem cells, the C/EBPα transcription factor actually declined after TLR ligation.

These results demonstrate that lymphoid biased progenitors can be driven to a DC fate by the MyD88-dependent TLR signals. Even though CLP express little TLR4/MD-2, LPS alters their differentiation with sufficient amounts of CD14. TLR signals suppress B lymphopoiesis and reveal the latent myeloid potential of lymphoid biased progenitors.

Exposure to LPS modulates the TLR4/MD-2 complex on hematopoietic progenitors in vivo. The above results showed that highly purified stem/progenitors can respond to TLR ligands in defined culture conditions. It was important to know if these phenomena pertain to progenitors in the bone marrow. LPS is known to cause a very rapid change in the TLR4/MD-2 complex, and this LPS-specific apparent conformational change results in diminished staining with a unique TLR4/MD-2 specific mAb (Akashi et al., 2003). The inventors exploited this phenomenon to ask if LPS can interact directly with hematopoietic progenitors in a physiological setting. First, whole bone marrow cells were stimulated with LPS in vitro and then stained with the mAb 1 h later (FIG. 8A). Mac-1$^+$ myeloid cells, Lin$^-$ and Lin$^-$ c-Kit$^+$ subsets of untreated marrow cells were clearly recognized by this mAb. In contrast, staining for TLR4/MD-2 was essentially negative after just 1 h of LPS exposure. The inventors then harvested bone marrow cells from intact mice treated with LPS or PBS (FIG. 8B). Remarkably, staining for TLR4/MD-2 was abolished by this short exposure to LPS.

Figure 15:
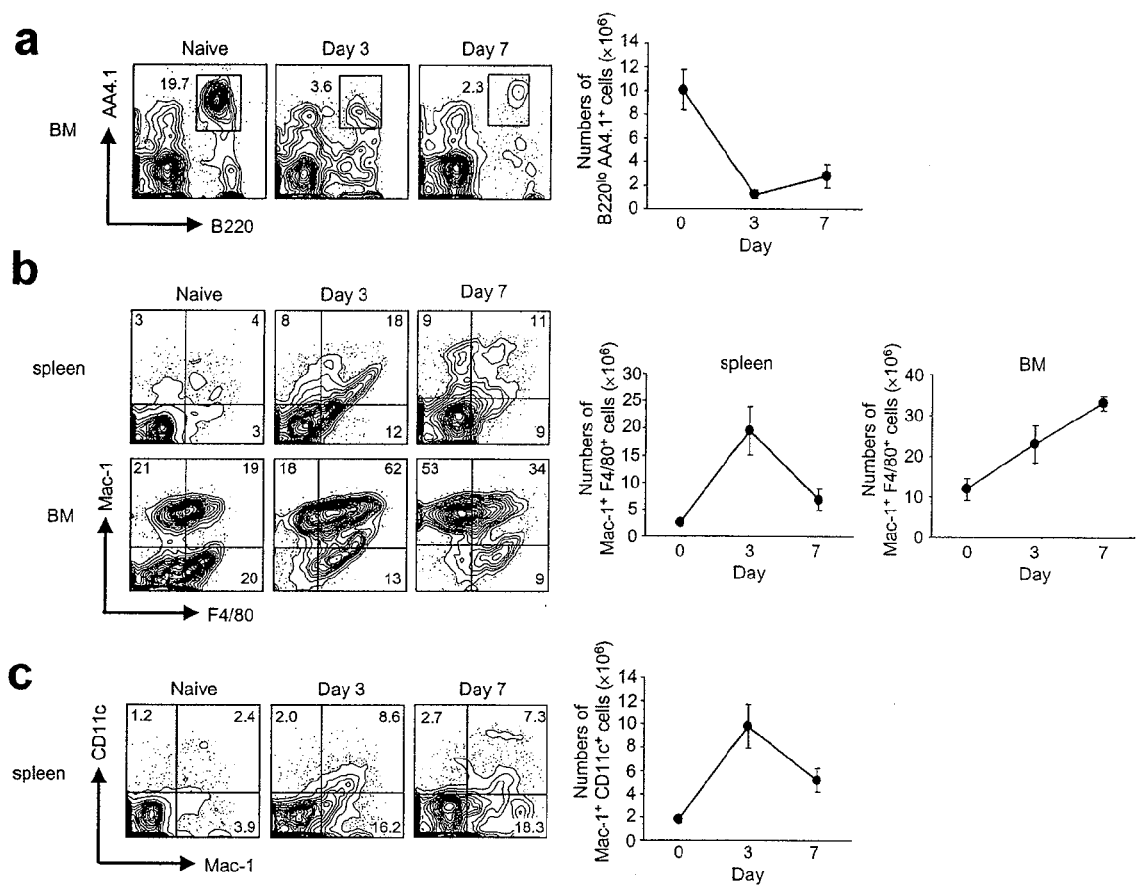
FIGS. 15A-C—Dramatic alterations in B lineage, monocytes/macrophages and dendritic cells in LPS treated mice. C57BL/6 mice were injected intraperitoneally with 100 μg LPS from *E. coli*. After 3 or 7 days, bone marrow cells from femurs and tibiae or spleen cells were stained with mAbs to indicated markers and analyzed by flow cytometry. Percentages of B220$^{lo}$ AA4.1+ (FIG. 15A), Mac-1+ F4/80+ (FIG. 15B), or Mac-1+ CD11c+ (FIG. 15C) cells are indicated. The graphs depict cell numbers of B220$^{lo}$ AA4.1+ (FIG. 15A), Mac-1+ F4/80+ (FIG. 15B), or Mac-1+ CD11c+ (FIG. 15C) cells. Data represent mean values with standard deviations from four mice and are representative of two independent experiments.

Bone marrow and spleens were then evaluated after LPS injection to determine if this treatment caused perturbations in hematopoietic cells. As has been noted in a previous study (Ueda et al., 2004), LPS depressed numbers of newly formed AA4.1$^+$ CD45R/B220$^+$ B lineage lymphocytes in the bone marrow (FIG. 15A). Reciprocally, numbers of CD11b/Mac-1$^+$ F4/80$^+$ monocytes/macrophages increased in the bone marrow and spleen (FIG. 7B). Increases were also recorded in numbers of CD11b/Mac-1$^+$ CD11c$^+$ myeloid DCs in spleen (FIG. 15C).

The inventors conclude that hematopoietic progenitors within bone marrow are directly and quickly affected by exposure to this TLR ligand. Changes in hematopoietic cells in vivo resemble the patterns of differentiation seen under highly defined conditions of culture.

Example 3

Discussion

Blood cell formation has traditionally been depicted as a series of branching steps, through which hematopoietic stems cells (HSCs) and their progeny sequentially lose differentiation options. However, it is now clear that this is a gradual process and progenitors in route to becoming one cell type retain other potential that can be revealed under particular circumstances. There are numerous examples where lymphoid lineage cells can be experimentally converted to macrophages (Kondo et al., 2000; Iwasaki-Arai et al., 2003; Xie et al., 2004). Until now, however, there has been no physiological basis for this phenomenon. In that context, it is interesting that plasmacytoid DCs can convert to myeloid DCs during viral infection (zuniga et al., 2004). A degree of lineage plasticity could provide a means to respond to microbial/viral products.

A key question is how TLR signals direct hematopoietic cells to a particular fate and obviate the need for normal environmental cytokines cues. Stem/progenitors from MyD88-deficient mice were unresponsive to two TLR ligands, so at least some of the previously described intracellular TLR signaling pathways are used. The MyD88-independent TRIF/TICAM pathway, which contributes to production of type I IFN (Ueda et al., 2004; Ueda et al., 2005), might not be important to the responses observed here. TLR stimulation of stem cells depressed SCL and GATA2 transcripts, while only slightly changing PU.1, but the inventors were surprised to find declines in the C/EBPα transcription factor that can drive macrophage differentiation (Rosmarin et al., 2005; Xie et al., 2004). Many of the other transcription factor changes were consistent with increased myeloid differentiation. The inventors considered the possibility that TLR ligands might stimulate hematopoietic cells to make their own factors. However, addition of neutralizing antibodies to M-CSF, GM-CSF, or TNFα provided no evidence for autocrine stimulation. Further experiments are required to exclude the potential contribution of other cytokines.

The results of stromal cell co-cultures initiated with single CLP extend those obtained in bulk, stromal cell-free cultures and would be consistent with either of two possible interpretations. TLR ligands could simultaneously suppress individual progenitors that are inherently biased for lymphopoiesis while stimulating those destined to produce DCs. Alternatively, single progenitors could be "reprogrammed" to adopt different fates as a result of TLR stimulation (Xie et al., 2004).

HSCs divide infrequently under normal circumstances, and retention of their unique potential for self-renewal may require residence in specialized niches near the endosteal surface (Zhang et al., 2003). Such an environment could protect the majority of stem cells from systemic events that would have potentially deleterious effects. An additional expectation is that stem cells express only those receptors needed to maintain their quiescence or allow them to actively differentiate as needed to replenish blood cell populations. Therefore, finding that functional TLRs and associated molecules are present at the stem cell stage was unexpected and raises the possibility that TLR ligands influence numbers and characteristics of stem cells in treated animals. Repeated infections could theoretically exhaust self-renewal potential or have other long-term consequences for the stem cell pool. Consequently, protective mechanisms may have evolved to block this response. Several negative regulators for TLR signaling have been reported that might work in a cell type-dependent manner (Liew et al., 2005). Furthermore, the RP105/MD-1 complex can be a negative regulator of TLR4 signaling on macrophages (Divanovic et al., 2005). It will therefore be important to learn if signals delivered via inhibitory molecules influence stem cell behavior. On the other hand, recognition that functional TLRs are expressed on stem/progenitors may suggest new ways to manipulate their activity for therapeutic purposes.

There is a huge body of literature concerning physiological responses to endotoxin shock (Beutler and Rietschel, 2003; Taylor et al., 2001). Multiple cell types respond to the many bacterial components, various cell types are re-distributed in the body, cytokines are released, and the coagulation system is activated. Dissecting discrete stimulatory pathways and mechanisms is extremely difficult in those circumstances. However, mobilization and re-distribution of hematopoietic cells in response to inflammatory processes has been known for some time (Ueda et al., 2004; Ueda et al., 2005). In experiments by the inventors, LPS injections depleted B lineage lymphocytes from bone marrow, as previously described by others (Ueda et al., 2004), and there were corresponding increases in macrophages and DCs. Multiple mechanisms may account for these changes but they are consistent with the responses of highly purified progenitors in defined culture conditions. The TLR4/MD-2 complex undergoes a rapid change on interaction with LPS such that staining with the MTS510 mAb is abolished (Akashi et al., 2003). The inventors exploited this response to learn that injected LPS diffuses into the bone marrow cavity and engages the receptors of stem cells/progenitors. This was the case for Lin$^-$ c-Kit$^+$ progenitors as well as Mac-1$^+$ myeloid cells (FIG. 8). Thus, these findings suggest that rapid interactions between foreign substances and hematopoietic progenitors could occur in bone marrow.

These new findings suggest that stem cells/progenitors need to be investigated from the perspective of disease-related processes. As just one example, full maturation of osteoclast progenitors is known to be altered by ligation of TLRs on hematopoietic cells[27,28]. An imbalance of osteoclast versus osteoblast activity and abnormal bone density might result from chronic microbial/viral infections. It is therefore important to learn if TLR expressing hematopoietic cells are involved in pathogenetic mechanisms.

In addition to the importance of TLRs in sensing pathogen-associated molecular patterns, a number of endogenous TLR ligands have been described (Tsan and Gao, 2004). Experimental TLR-dependent responses to these substances might have been due to trace contamination with bacterial products. However, the innate immune system could use this mechanism to sense danger represented by inflamed or remodeled tissues (Seong and Matzinger, 2004)[7]. The inventors are not aware of published descriptions of hematopoietic maturational defects in TLR gene targeted mice, but this could reflect functional redundancy among TLRs.

The Toll receptor was first discovered because of its importance to establishment of dorso/ventral polarity in *Drosophila* embryos, and it also has an immune function in that species (Ferrandon et al., 2004). Therefore, the results reported here indicate that TLRs may have developmental as well as immune roles that are highly conserved. Indeed, self/non-self discrimination may begin at the level of hematopoietic stem/progenitors, with TLRs instructing them to replenish the innate immune system.

Example 4

Stem Cell Engraftment

Figure 16:
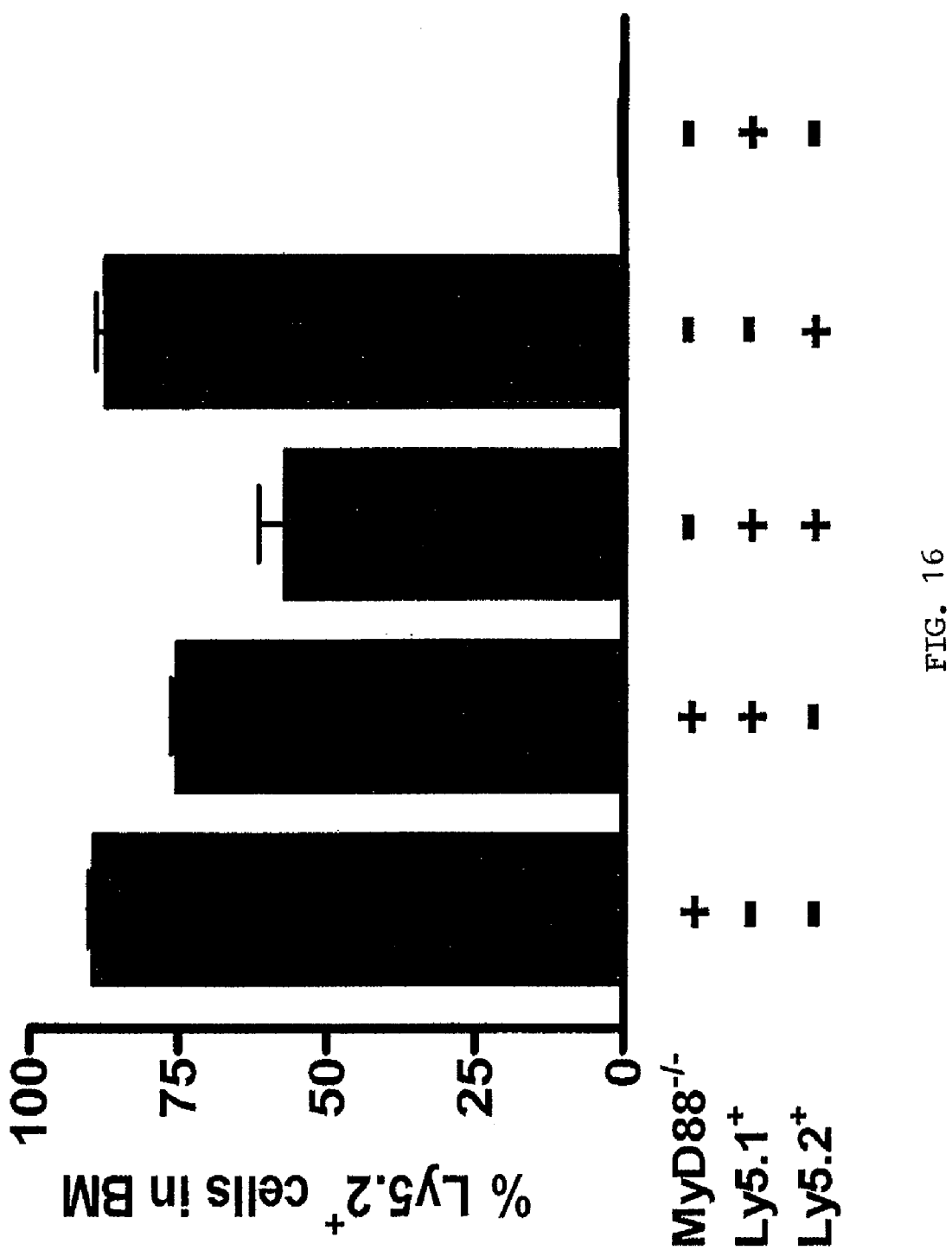
FIG. 16—MyD88$^{-/-}$ stem cells engraft better than those from normal mice. C57BL/6 (Ly5.1) mice were given a lethal dose of irradiation (650R×2) and then transplanted with a total of 2×10$^6$ bone marrow cells. Two of the five groups of experimental animals received a 50:50 mixture as indicated. The degree of chimerism in the marrow recipients was determined by flow cytometry 3 months following transplantation.

Bone marrow transplantation experiments were conducted to learn how hematopoietic progenitor cells of MyD88$^{-/-}$ mice function relative to those of normal mice. Bone marrow from MyD88$^{-/-}$ mice was transplanted along with bone marrow from MyD88$^{+/+}$ mice ($2 \times 10^6$ cells total) in a 1:1 ratio into C57BL/6 (Ly5.1) mice that had been given a lethal dose of irradiation (650 R×2). The degree of chimerism was determined by flow cytometry. Three months after the transplantation, most of the blood producing cells in the recipient bone marrow derived from the MyD88$^{-/-}$ cells (FIG. 16). Specifically, thymocytes and peripheral bood granulocytes were preferentially produced by MyD88$^{-/-}$ cells. The percentage of MyD88$^{-/-}$ lymphocytes in the spleen was closer to a 1:1 ratio, possibly because lymphocytes have long half lives, and their survival could partially depend on effective TLR signaling.

Example 5

Lymphoid Biased Progenitors Become Dendritic Cells

The inventors have demonstrated that lympho-hematopoietic cells respond to stimulation of TLR2 and TLR4 with lipopeptide and LPS, respectively. The findings were extended by showing that the cells express and utilize TLR9, a receptor for viruses and the ligand CpG ODN. Exposure of lymphoid progenitors to CpG ODN in vivo or in culture redirected them to become dendritic cells rather than lymphocytes.

They next asked if experimentally induced alterations in lymphoid versus dendritic cell production could be observed during viral infection. A dose of 1,000 PFU of human HSV-1 delivered by corneal scarification was selected because this causes an acute disease with 20% lethality at one week and multi-organ inflammation. Latent infection was studied in separate animals given 350 PFU and all of those animals survived at least 30 days. Pro-B, pre-B and B cells were all reduced in marrow of acutely infected mice, while pDC and IKDC were increased and there were no significant changes in cDC. No remarkable changes were found when mice with latent infections were examined at 30 days.

CLP were then recovered from HSV-1 infected mice and tested for differentiation potential in lymphoid cultures (FIG. 17A). The B lymphopoiesis was almost completely abolished in cells from acutely infected mice, while dendritic cell formation was very strongly favored. This was also apparent in terms of yield per input progenitor (FIG. 17B), while no abnormalities were found in CLP taken from animals with latent infections (FIG. 17C). The same disease model was then used with TLR9 gene targeted mice. Lymphoid and dendritic cells in bone marrow of mutant animals were refractory to acute infection. Furthermore, priming of lymphoid progenitors to dendritic fates was negligible when the TLR9 receptor was absent.

These observations demonstrate that hematopoietic cells express functional TLR9, and that the receptor mediates responses to acute viral infection. Therapeutic manipulation of TLR signaling may be advantageous for protecting stem cells in some circumstances and boosting replenishment of the innate immune system.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

X. REFERENCES

The following references, to the extent that they provide exemplary procedural or other details supplementary to those set forth herein, are specifically incorporated herein by reference.

U.S. Pat. No. 3,817,837
U.S. Pat. No. 3,826,364
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,284,412
U.S. Pat. No. 4,366,241
U.S. Pat. No. 4,472,509
U.S. Pat. No. 4,498,766
U.S. Pat. No. 4,661,913
U.S. Pat. No. 4,680,338
U.S. Pat. No. 4,714,682
U.S. Pat. No. 4,767,206
U.S. Pat. No. 4,774,189
U.S. Pat. No. 4,857,451
U.S. Pat. No. 4,938,948

U.S. Pat. No. 4,989,977
U.S. Pat. No. 5,021,236
U.S. Pat. No. 5,141,648
U.S. Pat. No. 5,160,974
U.S. Pat. No. 5,196,066
U.S. Pat. No. 5,478,722
U.S. Pat. No. 5,563,250
U.S. Pat. No. 5,856,456
U.S. Pat. No. 5,880,270
Akashi etal., *J Exp. Med.*, 198:1035-1042, 2003.
Akashi et al., *Nature*, 404:193-197, 2000.
Antibodies: A Laboratory Manual, Cold Spring Harbor Laboratory, 1988.
Arbibe et al., *Nat. Immunol.*, 1:533-540, 2000.
Atherton et al., *Biol. of Reproduction*, 32:155-171, 1985.
Bauer et al., *Proc Natl. Acad. Sci. USA*, 98:9237-9242, 2001.
Berberian et al., *Science*, 261:1588-1591, 1993.
Beutler, and Rietschel, *Nat. Rev. Immunol.*, 3:169-176, 2003.
Blander and Medzhitov, *Science*, 304:1014-1018, 2004.
Campbell, *In: Monoclonal Antibody Technology, Laboratory Techniques in Biochemistry and Molecular Biology*, Burden and Von Knippenberg (Eds.), 13:75-83, Amsterdam, Elseview, 1984.
Cario et al., *J Immunol.*, 164:966-972, 2000.
Casadevall et al., *Infect. Immun.*, 67:3703-3713, 1999.
Chaudhary etal., *Blood*, 91:4020-4027, 1998.
Christensen and Weissman, *Proc. Natl. Acad. Sci. USA*, 98:14541-14546, 2001.
Cleary et al., *Trends Microbiol.*, 4:131-136, 1994.
Dholakia et al., *J. Biol. Chem.*, 264, 20638-20642, 1989.
Divanovic et al., *Nat. Immunol.*, 6:571-578, 2005.
Doyle et al., *J Exp. Med.*, 199:81-90, 2004.
Du et al., *EurCytokine Network*, 11:362-371, 2000.
Ferrandon et al., *Semin. Immunol.*, 16:43-53, 2004.
Gay et al., *Nature*, 351:355-356, 1991.
Gefte et al., *Somatic Cell Genet.*, 3:231-236, 1977.
Geissmann et al., *Immunity*, 19:71-82, 2003.
Gilliet et al., *J Exp. Med.*, 195:953-958, 2002.
Goding, *In. Monoclonal Antibodies. Principles and Practice*, 2$^{nd}$ Ed., Orlando, Fla., Academic Press, 60-61, 65-66, 71-74, 1986.
Hayashi etal., *J. Immunol.*, 171:5130-5139, 2003.
Hayashi et al., *Nature*, 420:1099-1103, 2001.
Haynes et al, *J Virol.*, 75(22):10730-7, 2001.
Hemmi et al., *Nature*, 408:740-744, 2000.
Henderson and Calame, *Annu. Rev. Immunol.*, 16:163-200, 1998.
Heumann et al., *Curr. Opin. Microbiol.*, 1:49-55, 1998.
Hoshino et al., *J Immunol.*, 162:3749-3752, 1999.
Igarashi et al., *Immunity*, 17:117-130, 2002.
Iwasaki etal., *Immunity*, 19:451-462, 2003.
Iwasaki-Arai et al., *J Exp. Med.*, 197:1311-1322, 2003.
Janeway, *Immunol. Today*, 13:11-16, 1992.
Kadowaki et al., *J Exp. Med*, 194:863-869, 2001.
Kang et al., *Science*, 240:1034-1036, 1988.
Karsunky et al., *J Exp. Med.*, 198:305-313, 2003.
Kawada and Ogawa, *Blood*, 98:2008-2013, 2001.
Khatoon et al., *Ann. of Neurology*, 26, 210-219, 1989.
King etal., *J Biol. Chem.*, 269, 10210-10218, 1989.
Kimoto et al., *Scand J Infect Dis.* 35(9):568-72, 2003.
Kohler and Milstein, *Eur. J Immunol.*, 6:511-519, 1976.
Kohler and Milstein, *Nature*, 256:495-497, 1975.
Kohler etal., *Methods Enzymol.*, 178:3, 1989.
Kondo et al., *Cell*, 91:661-672, 1997.
Kondo et al., *Nature*, 407:383-386, 2000.
Kondo, et al., *Annu. Rev. Immunol.*, 21:759-806, 2003.
Kouro et al., *Blood*, 100:3672-3680, 2002.
Kreier et al., *In: Infection, Resistance and Immunity*, Harper and Row, New York, 1991.
Kreig, *Biochim. Biophys. Acta*, 1489:107-116, 1999.
Kurt-Jones etal., *Nat. Immunol.*, 1(5):398-401, 2000.
Lenert et al., *Science*, 248:1639-1643, 1990.
Liew et al., *Nat. Rev. Immunol.*, 5:446-458, 2005.
Liu et al., *Proc. Natl. Acad. Sci. USA*, 100:15824-15829, 2003.
Means et al., *Cytokine Growth Factor Rev.*, 11:219-232, 2000.
Means et al., *J Immunol.*, 163:6748-6755, 1999.
Medzhitov et al., *Mol. Cell*, 2:253-258, 1998.
Medzhitov et al., *Nature*, 388:394-397, 1997.
Miyake et al., *J Immunol.*, 161:1348-1353, 1998.
Nagai et al., *J Immunol.*, 174:7043-7049, 2005.
Nagai et al., *Nat. Immunol.*, 3:667-672, 2002.
Nagai, etal., *Blood*, 99:1699-1705, 2002.
Ohashi et al., *J Immunol.*, 164(2):558-561, 2000.
O'Neill et al., *Immunol. Today* 21:206-209, 2000.
O'Shannessy et al., *J Immun. Meth.*, 99, 153-161, 1987.
Oshiumi et al., *Nat. Immunol.*, 4:161-167, 2003.
Owens and Haley, *J Biol. Chem.*, 259:14843-14848, 1987.
Poltorak et al., *Science*, 282:2085-2088, 1998.
Potter and Haley, *Meth. in Enzymol.*, 91, 613-633, 1983.
Qureshietal., *J Exp. Med.*, 189:615-625, 1999.
Rosmarin et al., *Exp. Hematol.*, 33:131-143, 2005.
Sasso et al., *J Immunol.*, 142:2778-2783, 1989.
Sato et al., *J Exp. Med.*, 200:601-611, 2004.
Schroder et al., i J Immunol., 165:2683-2693, 2000.
Sedger et al., *J Immunol.*, 169:6193-6201, 2002.
Seong and Matzinger, *Nat. Rev. Immunol.*, 4:469-478, 2004.
Shigematsu et al., *Immunity*, 21:43-53, 2004.
Shimazuetal., *J Exp. Med.*, 189:1777-1782, 1999.
Shorki et al., *J Immunol*, 146:936-940, 1991.
Silvermann et al., *J Clin. Invest.*, 96:417-426, 1995.
Stein etal., *Cell*, 65:725-735, 1991.
Takeda and Akira, *Int. Immunol.*, 17:1-14, 2005.
Takeda et al., *Nat. Immunol.*, 5:987-995, 2004.
Takeuchi et al., *Gene*, 231:59-65, 1999.
Takeuchi et al., *Immunity*, 11:443-451, 1999.
Taylor et al., *Crit. Care Med.*, 29:326-334, 2001.
Tsan et al., *J Leukoc. Biol.*, 76:514-519, 2004.
Ueda et al., *J Exp. Med.*, 199:47-57, 2004.
Ueda et al., *J Exp. Med.*, 201:1771-1780, 2005.
Viriyakosol etal., *J Biol. Chem.*, 276:38044-38051, 2001.
Xie et al., *Cell*, 117:663-676, 2004.
Yamamoto et al., *Science*, 301:640-643, 2003.
Yang et al., *J Immunol.*, 163:639-643, 1999.
Yoshimura et al., *J Immunol.*, 163:1-5, 1999.
Zhang et al., *Nature*, 425:836-841, 2003.
Zuniga et al., *Nat. Immunol.*, 5:1227-1234, 2004.

What is claimed is:

1. A method for increasing the efficiency of hematopoietic stem cell engraftment after transplantation into a patient comprising inhibiting one or more toll-like receptor (TLR) pathways of hematopoietic stem cells in a cell graft by contacting said cell graft ex vivo with a TLR pathway antagonist and transplanting said cell graft into a patient, wherein the TLR pathway antagonist is a TLR9 or TLR4 antagonist and wherein the efficiency of hematopoietic stem cell engraftment in said patient is increased by TLR pathway antagonism of said hematopoietic stem cells.

2. The method of claim 1, wherein said cell graft is obtained from the patient.

3. The method of claim 1, wherein said cell graft is obtained from an allogeneic donor.

4. The method of claim 1, wherein the TLR9 or TLR4 antagonist is a soluble TLR, an anti-TLR antibody, or a soluble TLR dimerization mimic specific for TLR9 or TLR4.

5. The method of claim 1, wherein the TLR9 or TLR4 antagonist is an siRNA, ribozyme, morpholino oligo, or single chain Fv (scFv) or single chain antibody (scab) specific for TLR9 or TLR4.

6. The method of claim 1, wherein the TLR pathway is inhibited through inhibition of MyD88 expression.

7. The method of claim 1, wherein the antagonist acts on an MyD88-independent pathway.

8. The method of claim 7, wherein the antagonist acts on Toll/interleukin 1-like receptor domain-containing adapter-inducing interferon-β (TRIF) or TRIF-related adaptor molecule.

9. The method of claim 1, wherein said patient is immunocompromised or immunodeficient.

10. The method of claim 1, wherein said patient is being treated with chemotherapy.

11. The method of claim 1, wherein said patient has undergone an organ transplant.

12. The method of claim 1, wherein said patient is or has been administered an immunosuppressant.

13. The method of claim 1, wherein said patient suffers from an autoimmune disorder, or from another disorder or disease with an autoimmune component.

14. The method of claim 1, wherein said patient is a human.

* * * * *

UNITED STATES PATENT AND TRADEMARK OFFICE
CERTIFICATE OF CORRECTION

PATENT NO.        : 7,592,003 B2
APPLICATION NO.   : 11/537200
DATED             : September 22, 2009
INVENTOR(S)       : Yoshinori Nagai et al.

It is certified that error appears in the above-identified patent and that said Letters Patent is hereby corrected as shown below:

In claim 5, column 47, line 6, delete "scab" and insert --scAb-- therefor.

Signed and Sealed this

Seventeenth Day of November, 2009

David J. Kappos
*Director of the United States Patent and Trademark Office*